(12) United States Patent
Witt et al.

(10) Patent No.: US 9,820,868 B2
(45) Date of Patent: Nov. 21, 2017

(54) METHOD AND APPARATUS FOR A PIN APPARATUS

(71) Applicant: Biomet Manufacturing, LLC, Warsaw, IN (US)

(72) Inventors: Tyler D. Witt, Warsaw, IN (US); Austen Davenport, Columbia City, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 0 days.

(21) Appl. No.: 14/673,230

(22) Filed: Mar. 30, 2015

(65) Prior Publication Data

US 2016/0287408 A1 Oct. 6, 2016

(51) Int. Cl.
*A61F 2/32* (2006.01)
*A61F 2/34* (2006.01)
(Continued)

(52) U.S. Cl.
CPC ........ *A61F 2/4609* (2013.01); *A61B 17/8872* (2013.01); *A61F 2/34* (2013.01);
(Continued)

(58) Field of Classification Search
CPC ........ A61F 2/34; A61F 2/3401; A61F 2/4609; A61B 17/8897; A61B 17/1746; A61B 17/1666

See application file for complete search history.

(56) References Cited

U.S. PATENT DOCUMENTS 1,480,285 A 1/1924 Moore
2,181,746 A 11/1939 Siebrandt
(Continued)

FOREIGN PATENT DOCUMENTS

CA 2447694 A1 12/2002
CA 2501041 A1 4/2004
(Continued)

OTHER PUBLICATIONS

"International Application Serial No. PCT/US2016/024685, International Search Report dated Jun. 8, 2016", 6 pgs.
(Continued)

*Primary Examiner* — David Isabella
*Assistant Examiner* — Dinah Baria
(74) *Attorney, Agent, or Firm* — Schwegman Lundberg & Woessner, P.A.

(57) ABSTRACT

An acetabular guide system for placing a guide pin near an acetabulum, includes a patient specific acetabular guide including an interior surface and an exterior surface, the exterior surface being configured to have a geometry to register within the acetabulum of a specific patient, a first drill insert configured to be received by the guide at a first location, the first drill insert having a first longitudinal bore configured to be received concentrically in a guide bore of the guide, the guide bore extending exterior to the interior surface, a second drill insert configured to be fixed to a boney portion exterior to the acetabulum at a second location a predetermined distance from the first location, the second drill insert forming a second longitudinal bore, and a selectively removable alignment pin configured to be received by at least one of the first longitudinal bore and the second longitudinal bore.

20 Claims, 14 Drawing Sheets

(51) Int. Cl.
*A61F 2/46* (2006.01)
*A61B 17/17* (2006.01)
*A61B 17/88* (2006.01)
*A61B 17/56* (2006.01)
*A61B 34/10* (2016.01)

(52) U.S. Cl.
CPC ....... *A61B 17/1746* (2013.01); *A61B 17/8897* (2013.01); *A61B 2017/568* (2013.01); *A61B 2034/108* (2016.02)

(56) References Cited

U.S. PATENT DOCUMENTS

| | | |
|---|---|---|
| 2,407,845 A | 9/1946 | Nemeyer |
| 2,416,228 A | 2/1947 | Sheppard |
| 2,618,913 A | 11/1952 | Plancon et al. |
| 2,910,978 A | 11/1959 | Urist |
| 3,330,611 A | 7/1967 | Heifetz |
| 3,840,904 A | 10/1974 | Tronzo |
| 3,975,858 A | 8/1976 | Much |
| 4,246,895 A | 1/1981 | Rehder |
| 4,306,866 A | 12/1981 | Weissman |
| 4,324,006 A | 4/1982 | Charnley |
| 4,421,112 A | 12/1983 | Mains et al. |
| 4,436,684 A | 3/1984 | White |
| 4,457,306 A | 7/1984 | Borzone |
| 4,475,549 A | 10/1984 | Oh |
| 4,506,393 A | 3/1985 | Murphy |
| 4,524,766 A | 6/1985 | Petersen |
| 4,528,980 A | 7/1985 | Kenna |
| 4,565,191 A | 1/1986 | Slocum |
| 4,619,658 A | 10/1986 | Pappas et al. |
| 4,621,630 A | 11/1986 | Kenna |
| 4,632,111 A | 12/1986 | Roche |
| 4,633,862 A | 1/1987 | Petersen |
| 4,663,720 A | 5/1987 | Duret et al. |
| 4,689,984 A | 9/1987 | Kellner |
| 4,695,283 A | 9/1987 | Aldinger |
| 4,696,292 A | 9/1987 | Heiple |
| 4,703,751 A | 11/1987 | Pohl |
| 4,704,686 A | 11/1987 | Aldinger |
| 4,706,660 A | 11/1987 | Petersen |
| 4,719,907 A | 1/1988 | Banko et al. |
| 4,721,104 A | 1/1988 | Kaufman et al. |
| 4,722,330 A | 2/1988 | Russell et al. |
| 4,759,350 A | 7/1988 | Dunn et al. |
| 4,778,474 A | 10/1988 | Homsy |
| 4,800,874 A | 1/1989 | David et al. |
| 4,821,213 A | 4/1989 | Cline et al. |
| 4,822,365 A | 4/1989 | Walker et al. |
| 4,841,975 A | 6/1989 | Woolson |
| 4,846,161 A | 7/1989 | Roger |
| 4,871,975 A | 10/1989 | Nawata et al. |
| 4,892,545 A | 1/1990 | Day et al. |
| 4,893,619 A | 1/1990 | Dale et al. |
| 4,896,663 A | 1/1990 | Vandewalls |
| 4,907,577 A | 3/1990 | Wu |
| 4,927,422 A | 5/1990 | Engelhardt |
| 4,936,862 A | 6/1990 | Walker et al. |
| 4,952,213 A | 8/1990 | Bowman et al. |
| 4,959,066 A | 9/1990 | Dunn et al. |
| 4,976,737 A | 12/1990 | Leake |
| 4,979,949 A | 12/1990 | Matsen, III et al. |
| 4,985,037 A | 1/1991 | Petersen |
| 5,002,579 A | 3/1991 | Copf et al. |
| 5,006,121 A | 4/1991 | Hafeli |
| 5,007,936 A | 4/1991 | Woolson |
| 5,030,219 A | 7/1991 | Matsen, III et al. |
| 5,030,221 A | 7/1991 | Buechel et al. |
| 5,041,117 A | 8/1991 | Engelhardt |
| 5,053,035 A * | 10/1991 | McLaren ........... A61B 17/7208 606/62 |
| 5,053,037 A | 10/1991 | Lackey |
| 5,053,039 A | 10/1991 | Hofmann et al. |
| 5,056,351 A | 10/1991 | Stiver et al. |
| 5,086,401 A | 2/1992 | Glassman et al. |
| 5,098,383 A | 3/1992 | Hemmy et al. |
| 5,098,436 A | 3/1992 | Ferrante et al. |
| 5,108,425 A | 4/1992 | Hwang |
| 5,122,144 A | 6/1992 | Bert et al. |
| 5,123,927 A | 6/1992 | Duncan et al. |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,150,304 A | 9/1992 | Berchem et al. |
| 5,176,684 A | 1/1993 | Ferrante et al. |
| 5,194,066 A | 3/1993 | Van Zile |
| 5,234,433 A | 8/1993 | Bert et al. |
| 5,246,444 A | 9/1993 | Schreiber |
| 5,253,506 A | 10/1993 | Davis et al. |
| 5,258,032 A | 11/1993 | Bertin |
| 5,261,915 A | 11/1993 | Durlacher et al. |
| 5,274,565 A | 12/1993 | Reuben |
| 5,282,802 A | 2/1994 | Mahony, III |
| 5,299,288 A | 3/1994 | Glassman et al. |
| 5,300,077 A | 4/1994 | Howell |
| 5,320,529 A | 6/1994 | Pompa |
| 5,320,625 A | 6/1994 | Bertin |
| 5,323,697 A | 6/1994 | Schrock |
| 5,342,366 A | 8/1994 | Whiteside et al. |
| 5,344,423 A | 9/1994 | Dietz et al. |
| 5,360,446 A | 11/1994 | Kennedy |
| 5,364,402 A | 11/1994 | Mumme et al. |
| 5,368,858 A | 11/1994 | Hunziker |
| 5,370,692 A | 12/1994 | Fink et al. |
| 5,370,699 A | 12/1994 | Hood et al. |
| 5,405,395 A | 4/1995 | Coates |
| 5,408,409 A | 4/1995 | Glassman et al. |
| 5,411,521 A | 5/1995 | Putnam et al. |
| 5,415,662 A | 5/1995 | Ferrante et al. |
| 5,417,694 A | 5/1995 | Marik et al. |
| 5,438,263 A | 8/1995 | Dworkin et al. |
| 5,440,496 A | 8/1995 | Andersson et al. |
| 5,448,489 A | 9/1995 | Reuben |
| 5,449,360 A | 9/1995 | Schreiber |
| 5,452,407 A | 9/1995 | Crook |
| 5,454,816 A | 10/1995 | Ashby |
| 5,462,550 A | 10/1995 | Dietz et al. |
| 5,472,415 A | 12/1995 | King et al. |
| 5,474,559 A | 12/1995 | Bertin et al. |
| 5,490,854 A | 2/1996 | Fisher et al. |
| 5,496,324 A | 3/1996 | Barnes |
| 5,507,833 A | 4/1996 | Bohn |
| 5,514,519 A | 5/1996 | Neckers |
| 5,520,695 A | 5/1996 | Luckman |
| 5,527,317 A | 6/1996 | Ashby et al. |
| 5,539,649 A | 7/1996 | Walsh et al. |
| 5,540,695 A | 7/1996 | Levy |
| 5,545,222 A | 8/1996 | Bonutti |
| 5,549,688 A | 8/1996 | Ries et al. |
| 5,554,190 A | 9/1996 | Draenert |
| 5,560,096 A | 10/1996 | Stephens |
| 5,571,110 A | 11/1996 | Matsen, III et al. |
| 5,578,037 A | 11/1996 | Sanders et al. |
| 5,593,411 A | 1/1997 | Stalcup et al. |
| 5,595,703 A | 1/1997 | Swaelens et al. |
| 5,601,565 A | 2/1997 | Huebner |
| 5,607,431 A | 3/1997 | Dudasik et al. |
| 5,611,802 A | 3/1997 | Samuelson et al. |
| 5,613,969 A | 3/1997 | Jenkins, Jr. |
| 5,620,448 A | 4/1997 | Puddu |
| 5,634,927 A | 6/1997 | Houston et al. |
| 5,641,323 A | 6/1997 | Caldarise |
| 5,653,714 A | 8/1997 | Dietz et al. |
| 5,658,294 A | 8/1997 | Sederholm |
| 5,662,656 A | 9/1997 | White |
| 5,662,710 A | 9/1997 | Bonutti |
| 5,671,018 A | 9/1997 | Ohara et al. |
| 5,676,668 A | 10/1997 | McCue et al. |
| 5,677,107 A | 10/1997 | Neckers |
| 5,681,354 A | 10/1997 | Eckhoff |
| 5,682,886 A | 11/1997 | Delp et al. |
| 5,683,469 A | 11/1997 | Johnson et al. |

(56) References Cited

U.S. PATENT DOCUMENTS

| | | |
|---|---|---|
| 5,690,635 A | 11/1997 | Matsen, III et al. |
| 5,697,933 A | 12/1997 | Gundlapalli et al. |
| 5,702,460 A | 12/1997 | Carls et al. |
| 5,702,464 A | 12/1997 | Lackey et al. |
| 5,704,941 A | 1/1998 | Jacober et al. |
| 5,709,689 A | 1/1998 | Ferrante et al. |
| 5,720,752 A | 2/1998 | Elliott et al. |
| 5,722,978 A | 3/1998 | Jenkins, Jr. |
| 5,725,376 A | 3/1998 | Poirier |
| 5,725,593 A | 3/1998 | Caracciolo |
| 5,735,277 A | 4/1998 | Schuster |
| 5,745,834 A | 4/1998 | Bampton et al. |
| 5,748,767 A | 5/1998 | Raab |
| 5,749,875 A | 5/1998 | Puddu |
| 5,749,876 A | 5/1998 | Duvillier et al. |
| 5,762,125 A | 6/1998 | Mastrorio |
| 5,766,251 A | 6/1998 | Koshino et al. |
| 5,768,134 A | 6/1998 | Swaelens et al. |
| 5,769,092 A | 6/1998 | Williamson, Jr. |
| 5,776,200 A | 7/1998 | Johnson et al. |
| 5,786,217 A | 7/1998 | Tubo et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,835,619 A | 11/1998 | Morimoto et al. |
| 5,860,980 A | 1/1999 | Axelson, Jr. et al. |
| 5,860,981 A | 1/1999 | Bertin et al. |
| 5,871,018 A | 2/1999 | Delp et al. |
| 5,876,456 A | 3/1999 | Sederholm et al. |
| 5,879,398 A | 3/1999 | Swarts et al. |
| 5,879,402 A | 3/1999 | Lawes et al. |
| 5,880,976 A | 3/1999 | DiGioia, III et al. |
| 5,885,297 A | 3/1999 | Matsen, III |
| 5,885,298 A | 3/1999 | Herrington et al. |
| 5,888,219 A | 3/1999 | Bonutti |
| 5,895,389 A | 4/1999 | Schenk et al. |
| 5,899,907 A | 5/1999 | Johnson |
| 5,901,060 A | 5/1999 | Schall et al. |
| 5,911,724 A | 6/1999 | Wehrli |
| 5,921,988 A | 7/1999 | Legrand |
| 5,925,049 A | 7/1999 | Gustilo et al. |
| 5,942,370 A | 8/1999 | Neckers |
| 5,967,777 A | 10/1999 | Klein et al. |
| 5,976,149 A | 11/1999 | Masini |
| 5,980,526 A | 11/1999 | Johnson et al. |
| 6,008,433 A | 12/1999 | Stone |
| 6,019,767 A | 2/2000 | Howell |
| 6,033,415 A | 3/2000 | Mittelstadt et al. |
| 6,042,612 A | 3/2000 | Voydeville |
| 6,056,754 A | 5/2000 | Haines et al. |
| 6,059,789 A | 5/2000 | Dinger et al. |
| 6,059,833 A | 5/2000 | Doets |
| 6,066,175 A | 5/2000 | Henderson et al. |
| 6,086,593 A | 7/2000 | Bonutti |
| 6,120,510 A | 9/2000 | Albrektsson et al. |
| 6,120,544 A | 9/2000 | Grundei et al. |
| 6,126,690 A | 10/2000 | Ateshian et al. |
| 6,126,692 A | 10/2000 | Robie et al. |
| 6,136,033 A | 10/2000 | Suemer |
| 6,156,069 A | 12/2000 | Amstutz |
| 6,159,217 A | 12/2000 | Robie et al. |
| 6,161,080 A | 12/2000 | Aouni-Ateshian et al. |
| 6,162,257 A | 12/2000 | Gustilo et al. |
| 6,165,223 A | 12/2000 | Metzger et al. |
| 6,187,010 B1 | 2/2001 | Masini |
| 6,195,615 B1 | 2/2001 | Lysen |
| 6,203,546 B1 | 3/2001 | MacMahon |
| 6,205,411 B1 | 3/2001 | DiGioia, III et al. |
| 6,206,927 B1 | 3/2001 | Fell et al. |
| 6,210,445 B1 | 4/2001 | Zawadzki |
| 6,238,435 B1 | 5/2001 | Meulink et al. |
| 6,254,604 B1 | 7/2001 | Howell |
| 6,258,097 B1 | 7/2001 | Cook et al. |
| 6,264,698 B1 | 7/2001 | Lawes et al. |
| 6,270,529 B1 | 8/2001 | Terrill-Grisoni et al. |
| 6,273,891 B1 | 8/2001 | Masini |
| 6,290,727 B1 | 9/2001 | Otto et al. |
| 6,293,971 B1 | 9/2001 | Nelson et al. |
| 6,302,913 B1 | 10/2001 | Ripamonti et al. |
| 6,310,269 B1 | 10/2001 | Friese et al. |
| 6,312,258 B1 | 11/2001 | Ashman |
| 6,312,473 B1 | 11/2001 | Oshida |
| 6,319,285 B1 | 11/2001 | Chamier et al. |
| 6,322,728 B1 | 11/2001 | Brodkin et al. |
| 6,325,829 B1 | 12/2001 | Schmotzer |
| 6,327,491 B1 | 12/2001 | Franklin et al. |
| 6,338,738 B1 | 1/2002 | Bellotti et al. |
| 6,343,987 B2 | 2/2002 | Hayama et al. |
| 6,354,011 B1 | 3/2002 | Albrecht |
| 6,361,563 B2 | 3/2002 | Terrill-Grisoni et al. |
| 6,379,299 B1 | 4/2002 | Borodulin et al. |
| 6,379,388 B1 | 4/2002 | Ensign et al. |
| 6,383,228 B1 | 5/2002 | Schmotzer |
| 6,391,251 B1 | 5/2002 | Keicher et al. |
| 6,395,005 B1 | 5/2002 | Lovell |
| 6,413,279 B1 | 7/2002 | Metzger et al. |
| 6,424,332 B1 | 7/2002 | Powell |
| 6,427,698 B1 | 8/2002 | Yoon |
| 6,459,948 B1 | 10/2002 | Ateshian et al. |
| 6,463,351 B1 | 10/2002 | Clynch |
| 6,475,243 B1 | 11/2002 | Sheldon et al. |
| 6,482,236 B2 | 11/2002 | Habecker |
| 6,488,715 B1 | 12/2002 | Pope et al. |
| 6,503,255 B1 | 1/2003 | Albrektsson et al. |
| 6,508,980 B1 | 1/2003 | Sachs et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,519,998 B2 | 2/2003 | Ertl et al. |
| 6,520,964 B2 | 2/2003 | Tallarida et al. |
| 6,533,737 B1 | 3/2003 | Brosseau et al. |
| 6,547,823 B2 | 4/2003 | Scarborough et al. |
| 6,551,325 B2 | 4/2003 | Neubauer et al. |
| 6,554,837 B1 | 4/2003 | Hauri et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,562,073 B2 | 5/2003 | Foley |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,589,283 B1 | 7/2003 | Metzger et al. |
| 6,591,581 B2 | 7/2003 | Schmieding |
| 6,605,293 B1 | 8/2003 | Giordano et al. |
| 6,610,067 B2 | 8/2003 | Tallarida et al. |
| 6,622,567 B1 | 9/2003 | Hamel et al. |
| 6,629,999 B1 | 10/2003 | Serafin, Jr. |
| 6,641,617 B1 | 11/2003 | Merrill et al. |
| 6,676,892 B2 | 1/2004 | Das et al. |
| 6,682,566 B2 | 1/2004 | Draenert |
| 6,696,073 B2 | 2/2004 | Boyce et al. |
| 6,697,664 B2 | 2/2004 | Kienzle, III et al. |
| 6,701,174 B1 | 3/2004 | Krause et al. |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,749,638 B1 | 6/2004 | Saladino |
| 6,750,653 B1 | 6/2004 | Zou et al. |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,823,871 B2 | 11/2004 | Schmieding |
| 6,827,723 B2 | 12/2004 | Carson |
| 6,887,247 B1 | 5/2005 | Couture et al. |
| 6,905,514 B2 | 6/2005 | Carignan et al. |
| 6,916,324 B2 | 7/2005 | Sanford et al. |
| 6,923,817 B2 | 8/2005 | Carson et al. |

(56) References Cited

U.S. PATENT DOCUMENTS

| | | |
|---|---|---|
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |
| 6,975,755 B1 | 12/2005 | Baumberg |
| 6,990,220 B2 | 1/2006 | Ellis et al. |
| 6,993,406 B1 | 1/2006 | Cesarano, III et al. |
| 7,001,385 B2 | 2/2006 | Bonutti |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | McKinnon |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,121,832 B2 | 10/2006 | Hsieh et al. |
| 7,141,053 B2 | 11/2006 | Rosa et al. |
| D533,664 S | 12/2006 | Buttler et al. |
| 7,169,185 B2 | 1/2007 | Sidebotham |
| 7,174,282 B2 | 2/2007 | Hollister et al. |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | DiSilvestro et al. |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,291,177 B2 | 11/2007 | Gibbs |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,231 B2 | 2/2008 | McLean |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,390,327 B2 | 6/2008 | Collazo et al. |
| 7,392,076 B2 | 6/2008 | Moctezuma de La Barrera |
| 7,427,200 B2 | 9/2008 | Noble et al. |
| 7,427,272 B2 | 9/2008 | Richard et al. |
| 7,465,320 B1 | 12/2008 | Kito et al. |
| 7,468,075 B2 | 12/2008 | Lang et al. |
| 7,474,223 B2 | 1/2009 | Nycz et al. |
| 7,488,325 B2 | 2/2009 | Qian |
| 7,494,510 B2 | 2/2009 | Zweymuller |
| 7,517,365 B2 | 4/2009 | Carignan et al. |
| 7,519,540 B2 | 4/2009 | Mayaud |
| 7,527,631 B2 | 5/2009 | Maroney et al. |
| 7,534,263 B2 | 5/2009 | Burdulis, Jr. et al. |
| 7,537,664 B2 | 5/2009 | O'Neill et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kelman |
| 7,601,155 B2 | 10/2009 | Petersen |
| 7,603,192 B2 | 10/2009 | Martin et al. |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-Schaffer et al. |
| 7,651,501 B2 | 1/2010 | Penenberg et al. |
| 7,670,345 B2 | 3/2010 | Plassky et al. |
| 7,674,100 B2 | 3/2010 | Hayes-Pankhurst et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,704,253 B2 | 4/2010 | Bastian et al. |
| 7,723,395 B2 | 5/2010 | Ringeisen et al. |
| 7,747,305 B2 | 6/2010 | Dean et al. |
| D622,854 S | 8/2010 | Otto et al. |
| 7,780,672 B2 | 8/2010 | Metzger et al. |
| 7,780,740 B2 | 8/2010 | Steinberg |
| 7,789,885 B2 | 9/2010 | Metzger |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,833,245 B2 | 11/2010 | Kaes et al. |
| 7,837,040 B2 | 11/2010 | Ward et al. |
| 7,837,690 B2 | 11/2010 | Metzger |
| 7,846,382 B2 | 12/2010 | Strand et al. |
| 7,850,698 B2 | 12/2010 | Straszheim-Morley et al. |
| 7,879,109 B2 | 2/2011 | Borden et al. |
| 7,892,261 B2 | 2/2011 | Bonutti |
| 7,896,921 B2 | 3/2011 | Smith et al. |
| 7,926,363 B2 | 4/2011 | Miller et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,988,736 B2 | 8/2011 | May et al. |
| 7,993,353 B2 | 8/2011 | Rossner et al. |
| 8,062,301 B2 | 11/2011 | Ammann et al. |
| 8,066,708 B2 | 11/2011 | Lang et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,105,330 B2 | 1/2012 | Fitz et al. |
| 8,122,582 B2 | 2/2012 | Burdulis, Jr. et al. |
| 8,133,230 B2 | 3/2012 | Stevens et al. |
| 8,133,234 B2 | 3/2012 | Meridew et al. |
| 8,137,406 B2 | 3/2012 | Novak et al. |
| 8,147,861 B2 | 4/2012 | Jones et al. |
| 8,160,345 B2 | 4/2012 | Pavlovskaia et al. |
| 8,167,951 B2 | 5/2012 | Ammann et al. |
| 8,170,641 B2 | 5/2012 | Belcher |
| 8,182,489 B2 | 5/2012 | Horacek |
| 8,192,441 B2 | 6/2012 | Collazo |
| 8,192,495 B2 | 6/2012 | Simpson et al. |
| 8,200,355 B2 | 6/2012 | Lee et al. |
| 8,211,112 B2 | 7/2012 | Novak et al. |
| 8,221,430 B2 | 7/2012 | Park et al. |
| 8,241,292 B2 | 8/2012 | Collazo |
| 8,241,293 B2 | 8/2012 | Stone et al. |
| 8,246,680 B2 | 8/2012 | Betz et al. |
| 8,260,589 B1 | 9/2012 | Kumar |
| 8,265,790 B2 | 9/2012 | Amiot et al. |
| 8,268,099 B2 | 9/2012 | O'Neill et al. |
| 8,268,100 B2 | 9/2012 | O'Neill et al. |
| D669,176 S | 10/2012 | Frey |
| 8,282,646 B2 | 10/2012 | Schoenefeld et al. |
| 8,298,237 B2 | 10/2012 | Schoenefeld et al. |
| 8,303,596 B2 | 11/2012 | Plaßky et al. |
| 8,313,491 B2 | 11/2012 | Green, II et al. |
| D672,038 S | 12/2012 | Frey |
| 8,333,772 B2 | 12/2012 | Fox et al. |
| 8,337,503 B2 | 12/2012 | Lian |

(56) References Cited

U.S. PATENT DOCUMENTS

| | | |
|---|---|---|
| 8,355,773 B2 | 1/2013 | Leitner et al. |
| 8,372,078 B2 | 2/2013 | Collazo |
| 8,377,066 B2 | 2/2013 | Katrana et al. |
| 8,388,690 B2 | 3/2013 | Singhatat et al. |
| 8,398,646 B2 | 3/2013 | Metzger et al. |
| 8,407,067 B2 | 3/2013 | Uthgenannt et al. |
| 8,414,594 B2 | 4/2013 | Berger et al. |
| 8,419,741 B2 | 4/2013 | Carignan et al. |
| 8,425,522 B2 | 4/2013 | Bonutti |
| 8,430,882 B2 | 4/2013 | Lowry et al. |
| 8,430,931 B2 | 4/2013 | Acker et al. |
| 8,439,675 B2 | 5/2013 | De Moyer |
| 8,439,925 B2 | 5/2013 | Marino et al. |
| 8,444,564 B2 | 5/2013 | Mahfouz et al. |
| 8,444,651 B2 | 5/2013 | Kunz et al. |
| 8,457,930 B2 | 6/2013 | Schroeder |
| 8,460,302 B2 | 6/2013 | Park et al. |
| 8,469,961 B2 | 6/2013 | Alleyne et al. |
| 8,473,305 B2 | 6/2013 | Belcher et al. |
| 8,486,150 B2 | 7/2013 | White et al. |
| 8,500,740 B2 | 8/2013 | Bojarski et al. |
| 8,532,361 B2 | 9/2013 | Pavlovskaia et al. |
| 8,532,806 B1 | 9/2013 | Masson |
| 8,532,807 B2 | 9/2013 | Metzger |
| 8,535,387 B2 | 9/2013 | Meridew et al. |
| 8,543,234 B2 | 9/2013 | Gao |
| 8,545,508 B2 | 10/2013 | Collazo |
| 8,568,487 B2 | 10/2013 | Witt et al. |
| 8,591,516 B2 | 11/2013 | Metzger et al. |
| 8,597,365 B2 | 12/2013 | Meridew |
| 8,603,180 B2 | 12/2013 | White et al. |
| 8,608,748 B2 | 12/2013 | Metzger et al. |
| 8,608,749 B2 | 12/2013 | Meridew et al. |
| 8,617,170 B2 | 12/2013 | Ashby et al. |
| 8,617,174 B2 | 12/2013 | Axelson, Jr. et al. |
| 8,617,175 B2 | 12/2013 | Park et al. |
| 8,632,547 B2 | 1/2014 | Maxson et al. |
| 8,652,142 B2 | 2/2014 | Geissler |
| 8,668,700 B2 | 3/2014 | Catanzarite et al. |
| 8,702,712 B2 | 4/2014 | Jordan et al. |
| 8,702,715 B2 | 4/2014 | Ammann et al. |
| 8,706,285 B2 | 4/2014 | Narainasamy et al. |
| 8,715,289 B2 | 5/2014 | Smith |
| 8,728,387 B2 | 5/2014 | Jones et al. |
| 8,735,773 B2 | 5/2014 | Lang |
| 8,764,760 B2 | 7/2014 | Metzger et al. |
| 8,775,133 B2 | 7/2014 | Schroeder |
| 8,777,875 B2 | 7/2014 | Park |
| 8,828,016 B2 | 9/2014 | Major et al. |
| 8,828,087 B2 | 9/2014 | Stone et al. |
| 8,828,089 B1 | 9/2014 | Perez et al. |
| 8,834,568 B2 | 9/2014 | Shapiro |
| 8,858,561 B2 | 10/2014 | White et al. |
| 8,864,769 B2 | 10/2014 | Stone et al. |
| 8,900,244 B2 | 12/2014 | Meridew et al. |
| 8,903,530 B2 | 12/2014 | Metzger |
| 8,956,364 B2 | 2/2015 | Catanzarite et al. |
| 8,979,936 B2 | 3/2015 | White et al. |
| 9,005,297 B2 | 4/2015 | Katrana et al. |
| 2001/0005797 A1 | 6/2001 | Barlow et al. |
| 2001/0011190 A1 | 8/2001 | Park |
| 2001/0021876 A1 | 9/2001 | Terrill-Grisoni et al. |
| 2001/0054478 A1 | 12/2001 | Watanabe et al. |
| 2002/0007294 A1 | 1/2002 | Bradbury et al. |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0092532 A1 | 7/2002 | Yoon |
| 2002/0107522 A1 | 8/2002 | Picard et al. |
| 2002/0128872 A1 | 9/2002 | Giammattei |
| 2002/0147415 A1 | 10/2002 | Martelli |
| 2002/0186818 A1 | 12/2002 | Arnaud et al. |
| 2002/0193797 A1 | 12/2002 | Johnson et al. |
| 2002/0198528 A1 | 12/2002 | Engh et al. |
| 2002/0198531 A1 | 12/2002 | Millard et al. |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0039676 A1 | 2/2003 | Boyce et al. |
| 2003/0055502 A1 | 3/2003 | Lang et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0130741 A1 | 7/2003 | McMinn |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0054416 A1 | 3/2004 | Wyss et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122436 A1 | 6/2004 | Grimm |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0193169 A1 | 9/2004 | Schon et al. |
| 2004/0204644 A1 | 10/2004 | Tsougarakis et al. |
| 2004/0204760 A1 | 10/2004 | Fitz et al. |
| 2004/0212586 A1 | 10/2004 | Denny |
| 2004/0220583 A1 | 11/2004 | Pieczynski et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | de la Barrera |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0148843 A1 | 7/2005 | Roose |
| 2005/0149042 A1 | 7/2005 | Metzger |
| 2005/0171545 A1 | 8/2005 | Walsh et al. |

(56) References Cited

U.S. PATENT DOCUMENTS

| | | |
|---|---|---|
| 2005/0177245 A1 | 8/2005 | Leatherbury et al. |
| 2005/0203536 A1 | 9/2005 | Laffargue et al. |
| 2005/0203540 A1 | 9/2005 | Broyles |
| 2005/0209605 A1 | 9/2005 | Grimm et al. |
| 2005/0216305 A1 | 9/2005 | Funderud |
| 2005/0222571 A1 | 10/2005 | Ryan |
| 2005/0222573 A1 | 10/2005 | Branch et al. |
| 2005/0228393 A1 | 10/2005 | Williams et al. |
| 2005/0234461 A1 | 10/2005 | Burdulis et al. |
| 2005/0234465 A1 | 10/2005 | McCombs et al. |
| 2005/0234468 A1 | 10/2005 | Carson |
| 2005/0240195 A1 | 10/2005 | Axelson et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro et al. |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady et al. |
| 2006/0100832 A1 | 5/2006 | Bowman |
| 2006/0105011 A1 | 5/2006 | Sun et al. |
| 2006/0111722 A1 | 5/2006 | Bouadi |
| 2006/0122616 A1 | 6/2006 | Bennett et al. |
| 2006/0122618 A1 | 6/2006 | Claypool et al. |
| 2006/0136058 A1 | 6/2006 | Pietrzak |
| 2006/0142657 A1 | 6/2006 | Quaid et al. |
| 2006/0147332 A1 | 7/2006 | Jones et al. |
| 2006/0149283 A1 | 7/2006 | May et al. |
| 2006/0155380 A1 | 7/2006 | Clemow et al. |
| 2006/0161165 A1 | 7/2006 | Swanson |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0192319 A1 | 8/2006 | Solar |
| 2006/0195111 A1 | 8/2006 | Couture |
| 2006/0195194 A1 | 8/2006 | Gunther |
| 2006/0195198 A1 | 8/2006 | James |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak et al. |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0287891 A1 | 12/2006 | Grasso et al. |
| 2006/0293681 A1 | 12/2006 | Claypool et al. |
| 2007/0015995 A1 | 1/2007 | Lang et al. |
| 2007/0016008 A1 | 1/2007 | Schoenefeld |
| 2007/0016209 A1 | 1/2007 | Ammann et al. |
| 2007/0027680 A1 | 2/2007 | Ashley et al. |
| 2007/0039205 A1 | 2/2007 | Erb et al. |
| 2007/0043582 A1 | 2/2007 | Peveto et al. |
| 2007/0066917 A1 | 3/2007 | Hodorek et al. |
| 2007/0073133 A1 | 3/2007 | Schoenefeld |
| 2007/0073136 A1 | 3/2007 | Metzger |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0106299 A1 | 5/2007 | Manspeizer |
| 2007/0118055 A1 | 5/2007 | McCombs |
| 2007/0118138 A1 | 5/2007 | Seo et al. |
| 2007/0118243 A1 | 5/2007 | Schroeder et al. |
| 2007/0129809 A1 | 6/2007 | Meridew et al. |
| 2007/0142914 A1 | 6/2007 | Jones et al. |
| 2007/0150068 A1 | 6/2007 | Dong et al. |
| 2007/0156066 A1 | 7/2007 | McGinley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones et al. |
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor et al. |
| 2007/0239481 A1 | 10/2007 | DiSilvestro et al. |
| 2007/0244487 A1 | 10/2007 | Ammann et al. |
| 2007/0250169 A1 | 10/2007 | Lang |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288029 A1 | 12/2007 | Justin et al. |
| 2007/0288030 A1 | 12/2007 | Metzger et al. |
| 2008/0009952 A1 | 1/2008 | Hodge |
| 2008/0015599 A1 | 1/2008 | D'Alessio et al. |
| 2008/0015603 A1 | 1/2008 | Collazo |
| 2008/0015604 A1 | 1/2008 | Collazo |
| 2008/0015605 A1 | 1/2008 | Collazo |
| 2008/0021299 A1 | 1/2008 | Meulink |
| 2008/0021494 A1 | 1/2008 | Schmelzeisen-Redeker et al. |
| 2008/0021567 A1 | 1/2008 | Meulink et al. |
| 2008/0027563 A1 | 1/2008 | Johnson et al. |
| 2008/0033442 A1 | 2/2008 | Amiot et al. |
| 2008/0039850 A1 | 2/2008 | Rowley et al. |
| 2008/0051799 A1 | 2/2008 | Bonutti |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0094396 A1 | 4/2008 | Sabczynsdi et al. |
| 2008/0097451 A1 | 4/2008 | Chen et al. |
| 2008/0112996 A1 | 5/2008 | Harlow et al. |
| 2008/0114370 A1 | 5/2008 | Schoenefeld |
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |

(56) References Cited

U.S. PATENT DOCUMENTS

| | | |
|---|---|---|
| 2008/0147073 A1 | 6/2008 | Ammann et al. |
| 2008/0147074 A1 | 6/2008 | Ammann et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |
| 2008/0195099 A1 | 8/2008 | Minas |
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0255674 A1 | 10/2008 | Rahaman et al. |
| 2008/0257363 A1 | 10/2008 | Schoenefeld et al. |
| 2008/0262500 A1 | 10/2008 | Collazo |
| 2008/0262624 A1 | 10/2008 | White et al. |
| 2008/0269596 A1 | 10/2008 | Revie et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287926 A1 | 11/2008 | Abou El Kheir |
| 2008/0287954 A1 | 11/2008 | Kunz et al. |
| 2008/0294170 A1 | 11/2008 | O'Brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0024131 A1 | 1/2009 | Metzger et al. |
| 2009/0024169 A1 | 1/2009 | Triplett et al. |
| 2009/0043556 A1 | 2/2009 | Axelson et al. |
| 2009/0048618 A1 | 2/2009 | Harrison et al. |
| 2009/0066936 A1 | 3/2009 | Huang et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0076555 A1 | 3/2009 | Lowry et al. |
| 2009/0082770 A1 | 3/2009 | Worner et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |
| 2009/0116621 A1 | 5/2009 | Yuan et al. |
| 2009/0118736 A1 | 5/2009 | Kreuzer |
| 2009/0118769 A1 | 5/2009 | Sixto, Jr. et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149964 A1 | 6/2009 | May et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0209884 A1 | 8/2009 | Van Vorhis et al. |
| 2009/0209961 A1 | 8/2009 | Ferrante et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez et al. |
| 2009/0234360 A1 | 9/2009 | Alexander |
| 2009/0248044 A1 | 10/2009 | Amiot et al. |
| 2009/0250413 A1 | 10/2009 | Hoeppner |
| 2009/0254093 A1 | 10/2009 | White et al. |
| 2009/0254367 A1 | 10/2009 | Belcher et al. |
| 2009/0259312 A1 | 10/2009 | Shterling et al. |
| 2009/0270868 A1 | 10/2009 | Park et al. |
| 2009/0274350 A1 | 11/2009 | Pavlovskaia et al. |
| 2009/0287217 A1 | 11/2009 | Ammann et al. |
| 2009/0287309 A1 | 11/2009 | Walch et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2010/0010493 A1 | 1/2010 | Dower |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0036404 A1 | 2/2010 | Yi et al. |
| 2010/0042105 A1 | 2/2010 | Park et al. |
| 2010/0049195 A1 | 2/2010 | Park et al. |
| 2010/0057088 A1 | 3/2010 | Shah |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0082067 A1 | 4/2010 | Kondrashov |
| 2010/0087829 A1 | 4/2010 | Metzger et al. |
| 2010/0094295 A1 | 4/2010 | Schnieders et al. |
| 2010/0105011 A1 | 4/2010 | Karkar et al. |
| 2010/0121334 A1 | 5/2010 | Couture et al. |
| 2010/0121335 A1 | 5/2010 | Penenberg et al. |
| 2010/0137869 A1 | 6/2010 | Borja et al. |
| 2010/0137924 A1 | 6/2010 | Tuke et al. |
| 2010/0139377 A1 | 6/2010 | Huang et al. |
| 2010/0145343 A1 | 6/2010 | Johnson et al. |
| 2010/0145344 A1 | 6/2010 | Jordan et al. |
| 2010/0152782 A1 | 6/2010 | Stone et al. |
| 2010/0160917 A1 | 6/2010 | Fitz et al. |
| 2010/0160919 A1 | 6/2010 | Axelson, Jr. et al. |
| 2010/0168752 A1 | 7/2010 | Edwards |
| 2010/0168754 A1 | 7/2010 | Fitz et al. |
| 2010/0168857 A1 | 7/2010 | Hatch |
| 2010/0168866 A1 | 7/2010 | Shih |
| 2010/0179663 A1 | 7/2010 | Steinberg |
| 2010/0185202 A1 | 7/2010 | Lester et al. |
| 2010/0191244 A1 | 7/2010 | White et al. |
| 2010/0198067 A1 | 8/2010 | Mahfouz et al. |
| 2010/0198224 A1 | 8/2010 | Metzger et al. |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0217399 A1 | 8/2010 | Groh |

(56) References Cited

U.S. PATENT DOCUMENTS

| | | |
|---|---|---|
| 2010/0228257 A1 | 9/2010 | Bonutti |
| 2010/0249657 A1 | 9/2010 | Nycz et al. |
| 2010/0249796 A1 | 9/2010 | Nycz |
| 2010/0256649 A1 | 10/2010 | Capsal et al. |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0291401 A1 | 11/2010 | Medina et al. |
| 2010/0292743 A1 | 11/2010 | Singhal et al. |
| 2010/0298894 A1 | 11/2010 | Bojarski et al. |
| 2010/0305574 A1 | 12/2010 | Fitz et al. |
| 2010/0318088 A1 | 12/2010 | Warne et al. |
| 2010/0324692 A1 | 12/2010 | Uthgenannt et al. |
| 2011/0004317 A1 | 1/2011 | Hacking et al. |
| 2011/0008754 A1 | 1/2011 | Bassett et al. |
| 2011/0009869 A1 | 1/2011 | Marino et al. |
| 2011/0014081 A1 | 1/2011 | Jones et al. |
| 2011/0015636 A1 | 1/2011 | Katrana et al. |
| 2011/0015639 A1 | 1/2011 | Metzger et al. |
| 2011/0015752 A1 | 1/2011 | Meridew |
| 2011/0016690 A1 | 1/2011 | Narainasamy et al. |
| 2011/0022049 A1 | 1/2011 | Huebner et al. |
| 2011/0022174 A1 | 1/2011 | Holdstein et al. |
| 2011/0029088 A1 | 2/2011 | Rauscher et al. |
| 2011/0029091 A1 | 2/2011 | Bojarski et al. |
| 2011/0029093 A1 | 2/2011 | Bojarski et al. |
| 2011/0029116 A1 | 2/2011 | Jordan et al. |
| 2011/0035012 A1 | 2/2011 | Linares |
| 2011/0040303 A1 | 2/2011 | Iannotti |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0071581 A1 | 3/2011 | Lang et al. |
| 2011/0071802 A1 | 3/2011 | Bojarski et al. |
| 2011/0087332 A1 | 4/2011 | Bojarski et al. |
| 2011/0092804 A1 | 4/2011 | Schoenefeld et al. |
| 2011/0093086 A1 | 4/2011 | Witt et al. |
| 2011/0106093 A1 | 5/2011 | Romano et al. |
| 2011/0106254 A1 | 5/2011 | Abel et al. |
| 2011/0125264 A1 | 5/2011 | Bagga et al. |
| 2011/0125284 A1 | 5/2011 | Gabbrielli et al. |
| 2011/0130795 A1 | 6/2011 | Ball |
| 2011/0151027 A1 | 6/2011 | Clineff et al. |
| 2011/0151259 A1 | 6/2011 | Jarman-Smith et al. |
| 2011/0153025 A1 | 6/2011 | McMinn |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0177590 A1 | 7/2011 | Clyne et al. |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0214279 A1 | 9/2011 | Park et al. |
| 2011/0218545 A1 | 9/2011 | Catanzarite et al. |
| 2011/0224674 A1 | 9/2011 | White et al. |
| 2011/0238071 A1 | 9/2011 | Fernandez-Scoma |
| 2011/0245835 A1 | 10/2011 | Dodds et al. |
| 2011/0251617 A1 | 10/2011 | Ammann et al. |
| 2011/0257657 A1 | 10/2011 | Turner et al. |
| 2011/0269100 A1 | 11/2011 | Furrer et al. |
| 2011/0275032 A1 | 11/2011 | Tardieu et al. |
| 2011/0276145 A1 | 11/2011 | Carignan et al. |
| 2011/0282473 A1 | 11/2011 | Pavlovskaia et al. |
| 2011/0295887 A1 | 12/2011 | Palmese et al. |
| 2011/0313424 A1 | 12/2011 | Bono et al. |
| 2011/0319745 A1 | 12/2011 | Frey |
| 2012/0010619 A1 | 1/2012 | Barsoum |
| 2012/0010710 A1 | 1/2012 | Frigg |
| 2012/0010711 A1 | 1/2012 | Antonyshyn et al. |
| 2012/0029345 A1 | 2/2012 | Mahfouz et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0041564 A1 | 2/2012 | Landon |
| 2012/0065640 A1 | 3/2012 | Metzger et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0089595 A1 | 4/2012 | Jaecksch |
| 2012/0101586 A1 | 4/2012 | Carson |
| 2012/0109137 A1 | 5/2012 | Iannotti et al. |
| 2012/0109138 A1 | 5/2012 | Meridew et al. |
| 2012/0109226 A1 | 5/2012 | Iannotti et al. |
| 2012/0116203 A1 | 5/2012 | Vancraen et al. |
| 2012/0123422 A1 | 5/2012 | Agnihotri et al. |
| 2012/0130382 A1 | 5/2012 | Iannotti et al. |
| 2012/0136365 A1 | 5/2012 | Iannotti et al. |
| 2012/0141034 A1 | 6/2012 | Iannotti et al. |
| 2012/0143197 A1 | 6/2012 | Lang et al. |
| 2012/0143267 A1 | 6/2012 | Iannotti et al. |
| 2012/0150242 A1 | 6/2012 | Mannion |
| 2012/0158002 A1 | 6/2012 | Carignan et al. |
| 2012/0165954 A1 | 6/2012 | Nimal |
| 2012/0192401 A1 | 8/2012 | Pavlovskaia et al. |
| 2012/0196314 A1 | 8/2012 | Nawaz et al. |
| 2012/0209276 A1 | 8/2012 | Schuster |
| 2012/0215225 A1 | 8/2012 | Philippon et al. |
| 2012/0215310 A1 | 8/2012 | Sharp et al. |
| 2012/0221017 A1 | 8/2012 | Bonutti |
| 2012/0226283 A1 | 9/2012 | Meridew et al. |
| 2012/0232596 A1 | 9/2012 | Ribeiro |
| 2012/0245587 A1 | 9/2012 | Fang et al. |
| 2012/0259335 A1 | 10/2012 | Scifert et al. |
| 2012/0265208 A1 | 10/2012 | Smith |
| 2012/0271131 A1 | 10/2012 | Kling et al. |
| 2012/0271314 A1 | 10/2012 | Stemniski et al. |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289965 A1 | 11/2012 | Gelaude et al. |
| 2012/0296339 A1 | 11/2012 | Iannotti et al. |
| 2012/0303004 A1 | 11/2012 | Uthgenannt et al. |
| 2012/0303033 A1 | 11/2012 | Weiner et al. |
| 2012/0310364 A1 | 12/2012 | Li et al. |
| 2012/0310399 A1 | 12/2012 | Metzger |
| 2012/0316564 A1 | 12/2012 | Serbousek et al. |
| 2012/0323246 A1 | 12/2012 | Catanzarite et al. |
| 2012/0323282 A1 | 12/2012 | Brianza et al. |
| 2012/0323323 A1 | 12/2012 | Vargas et al. |
| 2013/0001121 A1 | 1/2013 | Metzger |
| 2013/0006250 A1 | 1/2013 | Metzger et al. |
| 2013/0018483 A1 | 1/2013 | Li et al. |
| 2013/0035766 A1 | 2/2013 | Meridew |
| 2013/0046310 A1 | 2/2013 | Ranawat et al. |
| 2013/0053854 A1 | 2/2013 | Schoenefeld et al. |
| 2013/0056912 A1 | 3/2013 | O'Neill et al. |
| 2013/0060253 A1 | 3/2013 | Couture et al. |
| 2013/0072940 A1 | 3/2013 | Dawood et al. |
| 2013/0085500 A1 | 4/2013 | Meridew et al. |
| 2013/0085590 A1 | 4/2013 | Bryan et al. |
| 2013/0119579 A1 | 5/2013 | Iannotti et al. |
| 2013/0123850 A1 | 5/2013 | Schoenefeld et al. |
| 2013/0131681 A1 | 5/2013 | Katrana et al. |
| 2013/0144392 A1 | 6/2013 | Hughes |
| 2013/0166034 A1* | 6/2013 | Landon ............... A61B 17/1675 623/20.2 |
| 2013/0197528 A1 | 8/2013 | Zakaria et al. |
| 2013/0197529 A1 | 8/2013 | Metzger et al. |
| 2013/0197687 A1 | 8/2013 | Pavlovskaia et al. |
| 2013/0218163 A1 | 8/2013 | Frey |
| 2013/0245631 A1 | 9/2013 | Bettenga |
| 2013/0245801 A1 | 9/2013 | Schroeder |
| 2013/0261503 A1 | 10/2013 | Sherman et al. |

(56) References Cited

U.S. PATENT DOCUMENTS

| | | |
|---|---|---|
| 2013/0264749 A1 | 10/2013 | Jones et al. |
| 2013/0268085 A1 | 10/2013 | Dong et al. |
| 2013/0289730 A1 | 10/2013 | Gabriel et al. |
| 2013/0317511 A1 | 11/2013 | Bojarski et al. |
| 2013/0326878 A1 | 12/2013 | Boehm et al. |
| 2013/0338673 A1 | 12/2013 | Keppler |
| 2014/0005672 A1 | 1/2014 | Edwards et al. |
| 2014/0012266 A1 | 1/2014 | Bonin, Jr. et al. |
| 2014/0052270 A1 | 2/2014 | Witt et al. |
| 2014/0066937 A1 | 3/2014 | Wiebe, III et al. |
| 2014/0081275 A1 | 3/2014 | Metzger et al. |
| 2014/0081659 A1 | 3/2014 | Nawana et al. |
| 2014/0088724 A1 | 3/2014 | Meridew |
| 2014/0094816 A1 | 4/2014 | White et al. |
| 2014/0100578 A1 | 4/2014 | Metzger et al. |
| 2014/0107651 A1 | 4/2014 | Meridew et al. |
| 2014/0107654 A1 | 4/2014 | Kehres et al. |
| 2014/0107715 A1 | 4/2014 | Heilman et al. |
| 2014/0127211 A1 | 5/2014 | Geles et al. |
| 2014/0135775 A1 | 5/2014 | Maxson et al. |
| 2014/0163564 A1 | 6/2014 | Bollinger |
| 2014/0163565 A1 | 6/2014 | Bollinger |
| 2014/0172116 A1 | 6/2014 | Maxson et al. |
| 2014/0188119 A1 | 7/2014 | Catanzarite et al. |
| 2014/0222157 A1 | 8/2014 | Al Hares et al. |
| 2014/0243831 A1 | 8/2014 | Witt |
| 2014/0243833 A1 | 8/2014 | Smith |
| 2014/0257304 A1 | 9/2014 | Eash |
| 2014/0257508 A1 | 9/2014 | Bojarski et al. |
| 2014/0276854 A1 | 9/2014 | Schoenefeld et al. |
| 2014/0276856 A1 | 9/2014 | Schoenefeld |
| 2014/0276870 A1 | 9/2014 | Eash |
| 2014/0276873 A1 | 9/2014 | Meridew et al. |
| 2014/0303938 A1 | 10/2014 | Schoenefeld et al. |
| 2014/0303990 A1 | 10/2014 | Schoenefeld et al. |
| 2014/0309644 A1 | 10/2014 | Metzger et al. |
| 2014/0324058 A1 | 10/2014 | Metzger et al. |
| 2014/0378979 A1 | 12/2014 | Stone et al. |
| 2015/0088293 A1 | 3/2015 | Metzger |
| 2015/0112348 A1 | 4/2015 | Schoenefeld et al. |
| 2015/0112349 A1 | 4/2015 | Schoenefeld |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 102038553 A | 5/2011 |
| CN | 102335742 A | 2/2012 |
| DE | 3447365 A1 | 7/1986 |
| DE | 04219939 | 12/1993 |
| DE | 4421153 A1 | 12/1995 |
| DE | 10341187 A1 | 3/2005 |
| DE | 102009028503 A1 | 2/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0255797 A1 | 2/1988 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1634551 A2 | 3/2006 |
| EP | 1832239 A1 | 9/2007 |
| EP | 1852072 A2 | 11/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| EP | 2502582 A1 | 9/2012 |
| EP | 2709568 A1 | 3/2014 |
| FR | 2659226 A1 | 9/1991 |
| FR | 2721195 A1 | 12/1995 |
| FR | 2768916 A1 | 4/1999 |
| FR | 2979817 A1 | 3/2013 |
| GB | 2094590 A | 9/1982 |
| GB | 2197790 A | 6/1988 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| JP | 59157715 A | 9/1984 |
| JP | 60231208 A | 11/1985 |
| JP | 6-233790 A | 8/1994 |
| JP | 2000245758 A | 9/2000 |
| JP | 2005-218861 A | 8/2005 |
| JP | 2009514612 A | 4/2009 |
| JP | 2011505080 A | 2/2011 |
| JP | 2011527885 A | 11/2011 |
| JP | 5710014 B2 | 4/2015 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| RU | 2218242 C2 | 12/2003 |
| TW | 231755 | 5/2005 |
| TW | 201114409 A | 5/2011 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-0226145 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051233 A2 | 6/2005 |
| WO | WO-2005051239 A1 | 6/2005 |
| WO | WO-2005051240 A1 | 6/2005 |
| WO | WO-2005077039 A2 | 8/2005 |
| WO | WO-2006058057 A2 | 6/2006 |
| WO | WO-2006060795 A1 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-2007041375 A2 | 4/2007 |

(56) References Cited

FOREIGN PATENT DOCUMENTS

| | | |
|---|---|---|
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009001109 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096553 A1 | 8/2010 |
| WO | WO-2010096557 A2 | 8/2010 |
| WO | WO-2010124164 A1 | 10/2010 |
| WO | WO-2010129870 A1 | 11/2010 |
| WO | WO-2010144705 A1 | 12/2010 |
| WO | WO-2010148103 A1 | 12/2010 |
| WO | WO-2010150223 A1 | 12/2010 |
| WO | WO-2011018458 A1 | 2/2011 |
| WO | WO-2011041398 A1 | 4/2011 |
| WO | WO-2011060536 A1 | 5/2011 |
| WO | WO-2011019797 A3 | 7/2011 |
| WO | WO-2011080260 A1 | 7/2011 |
| WO | WO-2011106711 A1 | 9/2011 |
| WO | WO-2011109260 A1 | 9/2011 |
| WO | WO-2011110374 A1 | 9/2011 |
| WO | WO-2011117644 A2 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012061042 A1 | 5/2012 |
| WO | WO-2012058353 A4 | 6/2012 |
| WO | WO-2012058355 A4 | 7/2012 |
| WO | WO-2012058349 A4 | 8/2012 |
| WO | WO-2012116206 A1 | 8/2012 |
| WO | WO-2012141790 A1 | 10/2012 |
| WO | WO-2012158917 A1 | 11/2012 |
| WO | WO-2012173929 A1 | 12/2012 |
| WO | WO-2012174008 A1 | 12/2012 |
| WO | WO-2013153401 A1 | 10/2013 |
| WO | WO-2013170872 A1 | 11/2013 |
| WO | WO-2014019712 A1 | 2/2014 |
| WO | WO-2014070889 A1 | 5/2014 |
| WO | WO-2015084831 A1 | 6/2015 |
| WO | WO-2016160788 A1 | 10/2016 |

OTHER PUBLICATIONS

"International Application Serial No. PCT/US2016/024685, Written Opinion dated Jun. 8, 2016", 7 pgs.
"Amazing Precision. Beautiful Results. The next evolution of MAKOplasty® is here," brochure. (Feb. 2009) MAKO Surgical Corp. 6 pages.
"Ascent Total Knee System," brochure. Biomet, Inc. (Oct. 31, 1999) 16 sheets.
"Comprehensive® Reverse Shoulder System Surgical Technique," Biomet Orthopedics brochure (2009-2012), 48 pages.
"Comprehensive® Reverse Shoulder System Technical Design Features," Biomet Orthopedics brochure (2009), 3 pages.
"Comprehensive® Reverse Shoulder System," Biomet Orthopedics brochure (2009), 8 pages.
"Comprehensive® Shoulder System Surgical Technique," Biomet Orthopedics brochure (2007), pp. 1-53.
"Comprehensive® Total Shoulder System," Biomet Orthopedics brochure (2011), 4 pages.
"Customized Patient Instruments, Patient specific instruments for patient specific needs," brochure. (2008) DePuy Orthopaedics, Inc. 14 sheets.
"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.
"Discovery® Elbow System Surgical Technique," brochure. Biomet Orthopedics, Inc. (Dec. 31, 2008) pp. 1-25.
"Discovery® Elbow System," brochure. Biomet Orthopedics, Inc. (Nov. 30, 2007) 3 sheets.
"Hipsextant Instructions of Use." (2011) Surgical Planning Associates, Inc. 19 pages.
"Is Subchondroplasty® Right for Me?" Retrieved from <http://www.subchondroplasty.com/about_subchondroplasty/is_subchondroplasty_right_for_>. . . Jul. 1, 2013, 1 sheet.
"Knee tensor combined with laser femoral head locator," Research Disclosure. Jul. 2006. No. 507; p. 903.
"Method for constructing an allograft sleeve." Research Disclosure (Dec. 2003) No. 476, p. 1294.
"OSS™ Orthopaedic Salvage System, Femoral/Tibial Augmentation," brochure. Biomet Orthopedics, Inc., (Mar. 31, 2004) pp. 1-8 (12 sheets).
"Patient Matched PMI Implants, C.A.M.R.A. 3-D Imaging," brochure, Biomet, Inc. (Jan. 31, 1991) 6 pages.
"Regenerex® Tibial Cone Augment, Surgical Technique Addendum to the Vanguard® SSK Revision System," brochure. Biomet® Orthopedics. (Mar. 31, 2010) pp. 1-8 (12 sheets).
"Signature™ Personalized Patient Care, Surgical Technique Addendum to the Vanguard Knee System" brochure. Biomet® Orthopedics, Inc. (May 15, 2009) pp. 1-8.
"Subchondroplasty," Retrieved from <http://www.subchondroplasty.com/>. Jul. 1, 2013. 1 sheet.
"TruMatch™ Personalized knee replacement solutions," tri-fold brochure. (2009) SIGMA® DePuy Orthopaedics, Inc. 2 pages.
"Vanguard® PFR Partial Knee Patellofemoral Replacement System," Surgical Technique brochure. Biomet Orthopaedics, (Aug. 31, 2010) pp. 1-25.
"Zimmer® UniSpacer® Knee System," brochure. (2005) Zimmer, Inc. 4 sheets.
Biomet "Oxford® Partial Knee" brochure, 8 pages (Feb. 2011).
Biomet "The Oxford® Partial Knee Surgical Technique," brochure, pp. 1-38, (Feb. 2010).
Biomet, "Oxford® Partial Knee Microplasty® Instrumentation Surgical Technique", brochure, pp. 1-54 (May 2011).
Birnbaum, Klaus, M.D., "Computer-Assisted Orthopedic Surgery With Individual Templates and Comparison to Conventional Method," SPINE vol. 26, No. 4, pp. 365-370 (2001) Lippincott Williams & Wilkins, Inc.
Botha, Charl P., Technical Report: DeVIDE—The Delft Visualisation and Image processing Development Environment, pp. 1-49 (May 31, 2006).
Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.
Deakon, Timothy, MD, Posterior Cruciate Ligament Reconstruction Technique Using the Modular ACL/PCL Guide Rationale and Surgical Technique, Arthrotek®, a Biomet Company. (2003). (6 pages).
Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.
European Communication Pursuant to Article 94(3) EPC dated Jan. 22, 2015 for PCT/US2007/013223 filed Jun. 5, 2007, which claims benefit of U.S. Appl. No. 60/812,694, filed Jun. 9, 2006 and U.S. Appl. No. 11/756,057, filed May 31, 2007.
European Communication Pursuant to Article 94(3) EPC dated Feb. 4, 2015 for PCT/US2010/024584 filed Feb. 18, 2010, which claims benefit of U.S. Appl. No. 12/389,901, filed Feb. 20, 2009.

(56) References Cited

OTHER PUBLICATIONS

European Communication Pursuant to Article 94(3) EPC dated Feb. 10, 2015 for PCT/US2009/039507 filed Apr. 3, 2009, which claims benefit of U.S. Appl. No. 12/103,824, filed Apr. 16, 2008.
European Communication Pursuant to Article 94(3) EPC dated Nov. 24, 2014 for PCT/US2012/038351 which claims benefit of U.S. Appl. No. 13/111,007, filed May 19, 2011.
Farr, J., Cole, B. , Kercher, J., Batty, L. and Bajaj, S., Anteromedial Tibial Tubercle Osteotomy (Fulkerson Osteotomy). Re-print from V. Sanchis-Alfonso (ed), Anterior Knee Pain and patellar Instability, DOI: 10.1007/978-0-85729-507-1_40, © Springer-Verlag London Limited 2011.(9 pages).
Farr, J., Fulkerson, J. Surgical Technique for Anteromedialization of the Tibial Tubercle with the Tracker™ AMZ Guide System. Sports Medicine and Arthroscopy Review, vol. 2, No. 3, 1994. (12 pages).
Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.
Friedman, R.J. et al., "The Use of Computerized Tomography in the Measurement of Glenoid Version", Journal of Bone & Joint Surgery Am. (JBJS) 1992;74:1032-1037 (Aug. 1992).
Great Britain Search Report dated Dec. 21, 2011 for GB1116054.6, claiming benefit of U.S. Appl. No. 12/888,005, filed Sep. 22, 2010.
Haaker, R.G., et al., "Minimal-invasive navigiert implantierte unikondyläre Knieendoprothese," Orthopäde 2006 35:1073-1079 (Sep. 13, 2006) Spinger Medizin Verlag.
Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.
Hazan, Eric J., M.D., "Computer-Assisted Orthopaedic Sugery, A New Paradigm," Techniques in Orthopaedics® vol. 18, No. 2, (2003) pp. 221-229.
Hutmacher, Dietmar, W., "Scaffolds in tissue engineering bone and cartilage," Biomaterials, 2000 Elsevier Science Ltd. (pp. 2529-2543).
International Preliminary Report and Written Opinion dated Jan. 5, 2012 for PCT/US2010/038845 claiming benefit of U.S. Appl. No. 12/486,992, filed Jun. 18, 2009.
International Preliminary Report on Patentability and Written Opinion for PCT/US2009/039578 dated Oct. 28, 2010 claiming benefit of U.S. Appl. No. 12/103,834, filed Apr. 16, 2008.
International Preliminary Report on Patentability and Written Opinion dated Apr. 24, 2014 for PCT/US2012/059189 claiming benefit of U.S. Appl. No. 13/597,478, filed Aug. 29, 2012.
International Preliminary Report on Patentability and Written Opinion dated Dec. 22, 2011 for PCT/US2010/038177 claiming benefit of U.S. Appl. No. 12/483,807, filed Jun. 12, 2009.
International Preliminary Report on Patentability and Written Opinion dated Jan. 3, 2014 for PCT/US2012/042081 claiming benefit of U.S. Appl. No. 13/493,509, filed Jun. 11, 2012.
International Preliminary Report on Patentability and Written Opinion dated Mar. 13, 2014 for PCT/US2012/052853 claiming benefit of U.S. Appl. No. 13/221,968, filed Aug. 31, 2011.
International Preliminary Report on Patentability and Written Opinion dated May 8, 2014 for PCT/US2012/060842 claiming benefit of U.S. Appl. No. 13/653,868, filed Oct. 17, 2012.
International Preliminary Report on Patentability and Written Opinion dated May 8, 2014 for PCT/US2012/060848 claiming benefit of U.S. Appl. No. 13/653,878, filed Oct. 17, 2012.
International Preliminary Report on Patentability and Written Opinion dated May 8, 2014 for PCT/US2012/060853 claiming benefit of U.S. Appl. No. 13/653,886, filed Oct. 17, 2012.
International Preliminary Report on Patentability and Written Opinion dated May 8, 2014 for PCT/US2012/060854 claiming benefit of U.S. Appl. No. 13/653,893, filed Oct. 17, 2012.
International Preliminary Report on Patentability and Written Opinion dated Nov. 28, 2013 for PCT/US2012/038351 claiming benefit of U.S. Appl. No. 13/111,007, filed May 19, 2011.
International Preliminary Report on Patentability and Written Opinion dated Oct. 28, 2010 for PCT/US2009/039507 claiming benefit of U.S. Appl. No. 12/103,824, filed Apr. 16, 2008.
International Preliminary Report on Patentability and Written Opinion dated Mar. 12, 2015 for PCT/US2013/057097 claiming benefit of U.S. Appl. No. 13/597,478, filed Aug. 29, 2012.
International Preliminary Report on Patentability and Written Opinion dated May 14, 2015 for PCT/US2013/067505 claiming benefit of U.S. Appl. No. 13/718,129, filed Dec. 18, 2012.
International Preliminary Report on Patentability and Written Opinion dated Sep. 7, 2012 for PCT/US2011/026333 claiming benefit of U.S. Appl. No. 12/714,023, filed Feb. 26, 2010.
International Preliminary Report on Patentability for PCT/US2007/013223 dated Dec. 24, 2008 claiming benefit of U.S. Appl. No. 11/756,057, filed May 31, 2007.
International Preliminary Report on Patentability for PCT/US2010/050701 dated Apr. 12, 2012 claiming benefit of U.S. Appl. No. 12/571,969, filed Oct. 1, 2009.
International Preliminary Report on Patentability dated Aug. 25, 2011 for PCT/US2010/024073 filed Feb. 12, 2010, claiming benefit of U.S. Appl. No. 12/371,096, filed Feb. 13, 2009.
International Preliminary Report on Patentability dated Mar. 31, 2011 for PCT/US2009/056670 claiming benefit of U.S. Appl. No. 12/211,407, filed Sep. 16, 2008.
International Preliminary Report on Patentability dated Sep. 1, 2011 for PCT/US2010/024579 claiming benefit of U.S. Appl. No. 12/389,930, filed Feb. 20, 2009.
International Preliminary Report on Patentability dated Sep. 1, 2011 for PCT/US2010/024584 claiming benefit of U.S. Appl. No. 12/389,901, filed Feb. 20, 2009.
International Preliminary Report on Patentability dated Sep. 6, 2013 for PCT/US2012/026356 claiming benefit of U.S. Appl. No. 13/041,883, filed Mar. 7, 2011.
International Preliminary Report on Patentability Report and Written Opinion dated Sep. 4, 2014 for PCT/US2013/026875 claiming benefit of U.S. Appl. No. 13/400,652, filed Feb. 21, 2012.
International Search Report and Written Opinion for PCT/US2007/013223 dated Nov. 26, 2007, claiming benefit of U.S. Appl. No. 11/756,057, filed May 31, 2007.
International Search Report and Written Opinion for PCT/US2009/039507 dated Jul. 14, 2009, claiming benefit of U.S. Appl. No. 12/103,824, filed Apr. 16, 2008.
International Search Report and Written Opinion for PCT/US2009/056670 dated Mar. 2, 2010 claiming benefit of U.S. Appl. No. 12/211,407, filed Sep. 16, 2008.
International Search Report and Written Opinion for PCT/US2013/026875 dated Jun. 7, 2013, claiming benefit of U.S. Appl. No. 13/400,652, filed Feb. 21, 2012.
International Search Report and Written Opinion dated Apr. 14, 2014 for PCT/US2013/067505 claiming benefit of U.S. Appl. No. 13/718,129, filed Dec. 18, 2012.
International Search Report and Written Opinion dated Apr. 22, 2010 for PCT/US2010/024579 claiming benefit of U.S. Appl. No. 12/389,930, filed Feb. 20, 2009.
International Search Report and Written Opinion dated Aug. 19, 2010 for PCT/US2010/024584 claiming benefit of U.S. Appl. No. 12/389,901, filed Feb. 20, 2009.
International Search Report and Written Opinion dated Aug. 24, 2010 for PCT/US2010/038177 claiming benefit of U.S. Appl. No. 12/483,807, filed Jun. 12, 2009.
International Search Report and Written Opinion dated Aug. 9, 2011 for PCT/US2011/026333 claiming benefit of U.S. Appl. No. 12/714,023, filed Feb. 26, 2010.
International Search Report and Written Opinion dated Dec. 18, 2012 for PCT/US2012/059189, which claims benefit of U.S. Appl. No. 13/597,478, filed Aug. 29, 2011.
International Search Report and Written Opinion dated Dec. 7, 2010 for PCT/US2010/050701 claiming benefit of U.S. Appl. No. 12/571,969, filed Oct. 1, 2009.
International Search Report and Written Opinion dated Feb. 6, 2013 for PCT/US2012/060842, which claims benefit of U.S. Appl. No. 13/653,868, filed Oct. 17, 2012.

(56) References Cited

OTHER PUBLICATIONS

International Search Report and Written Opinion dated Feb. 6, 2013 for PCT/US2012/060854, which claims benefit of U.S. Appl. No. 13/653,893, filed Oct. 17, 2012.
International Search Report and Written Opinion dated Jul. 10, 2014 for PCT/US2014/023655 claiming benefit of U.S. Appl. No. 13/800,369, filed Mar. 13, 2013.
International Search Report and Written Opinion dated Jul. 31, 2009 for PCT/US2009/039578 claiming benefit of U.S. Appl. No. 12/103,834, filed Apr. 16, 2008.
International Search Report and Written Opinion dated Jun. 24, 2014 for PCT/US2014/022000 claiming benefit of U.S. Appl. No. 13/889,869, filed May 8, 2013.
International Search Report and Written Opinion dated Jun. 4, 2010 for PCT/US2010/024073 filed Feb. 12, 2010, claiming benefit of U.S. Appl. No. 12/371,096, filed Feb. 13, 2009.
International Search Report and Written Opinion dated Mar. 5, 2012 for PCT/US2011/057300 claiming benefit of U.S. Appl. No. 12/938,905, filed Nov. 3, 2010.
International Search Report and Written Opinion dated May 23, 2014 for PCT/US2013/074288 claiming benefit of U.S. Appl. No. 13/790,770, filed Mar. 8, 2013, which priority is also claimed of U.S. Appl. No. 13/711,306, filed Dec. 11, 2012.
International Search Report and Written Opinion dated May 8, 2012 for PCT/US2012/026356 claiming benefit of U.S. Appl. No. 13/041,883, filed Mar. 7, 2011.
International Search Report and Written Opinion dated May 9, 2011 for PCT/US2011/026412 claiming benefit of U.S. Appl. No. 12/872,663, filed Aug. 31, 2010.
International Search Report and Written Opinion dated Nov. 15, 2012, for PCT/US2012/052853, which claims benefit of U.S. Appl. No. 13/221,968, filed Aug. 31, 2011.
International Search Report and Written Opinion dated Oct. 14, 2013 for PCT/US2013/057097 claiming benefit of U.S. Appl. No. 13/597,478, filed Aug. 29, 2012.
International Search Report and Written Opinion dated Oct. 5, 2010 for PCT/US2010/038845 claiming benefit of U.S. Appl. No. 12/486,992, filed Jun. 18, 2009.
International Search Report and Written Opinion dated May 8, 2015 for PCT/US2014/068131 claiming benefit of U.S. Appl. No. 13/095,565, filed Dec. 3, 2013.
International Search Report dated Nov. 30, 2010 for PCT/EP2010/061630 filed Aug. 10, 2010 claiming benefit of DE102009028503.2 filed Aug. 13, 2009.
International Search Report dated Oct. 23, 2012, for PCT/US2012/041893, which claims benefit of U.S. Appl. No. 61/496,177, filed Jun. 13, 2011.
Invitation to Pay Additional Fees dated Feb. 6, 2013 for PCT/US2012/060848, which claims benefit of U.S. Appl. No. 13/653,878, filed Oct. 17, 2012.
Invitation to Pay Additional Fees dated Feb. 6, 2014 for PCT/US2013/067505, which claims benefit of U.S. Appl. No. 13/718,129, filed Dec. 18, 2012.
Invitation to Pay Additional Fees dated Feb. 7, 2013 for PCT/US2012/060853, which claims benefit of U.S. Appl. No. 13/653,893, filed Oct. 17, 2012.
Invitation to Pay Additional Fees dated May 3, 2011 for PCT/US2011/026333 claiming benefit of U.S. Appl. No. 12/714,023, filed Feb. 26, 2010.
Invitation to Pay Additional Fees with Partial International Search dated Nov. 26, 2009 for PCT/US2009/056670.
Japanese Office Action dated Apr. 7, 2015 for PCT/US2012/038351 filed May 17, 2012 claiming benefit of U.S. Appl. No. 13/111,007, filed May 19, 2011.
K. Subburaj et al., "Automated 3D Geometric Reasoning in Computer Assisted Joint Reconstructive Surgery", IEEE International Conference on Automation Science and Engineering, Publication Year: 2009, pp. 367-372.
Kaus, Michael R., Ph.D., "Automated Segmentation of MR Images of Brain Tumors," Radiology, vol. 218, No. 2, (2001) pp. 586-591.

Kelly, Todd C., M.D., "Role of Navigation in Total Hip Arthroplasty." The Journal of Bone & Joint Surgery(2009) pp. 153-158. vol. 91-A, Supplement 1.
Klein, M., "Robot assisted insertion of craniofacial implants—clinical experience," CARS 2001, pp. 133-138 (2001) Elsevier Science B.V.
Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.
Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.
Murphy, S.B., et al. "The Hip Sextant: Navigation of Acetabular Component Orientation Using a Mechanical Instrument," brochure. (2009) 1 page.
Nicholls, Paul, M.D., "Trauma Grand Rounds PMI (Patient-Matched Implants)" brochure, Biomet Orthopedics, Inc., (Feb. 29, 2000) 1 page.
Overhoff, H.M., et al., "Total Knee Arthroplasty: Coordinate System Definition and Planning based on 3-D Ultrasound Image Volumes," CARS 2001, pp. 283-288, (2001) Elsevier Science B.V.
Patent Examiniation Report No. 1 dated Feb. 16, 2015 for PCT/US2013/026875 filed Feb. 20, 2013, which claims benefit of U.S. Appl. No. 13/400,652, filed Feb. 21, 2012.
Portheine, F., "CT-basierte Planung und DISOS-Schablonennavigation in der Kniegelenkendoprothetik," in Navigation und Robotic in der Gelenk—und Wirbelsäulenchirugie, Kapitel 32, Springer Verlag (2003) pp. 262-269.
Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.
Portheine, K., "Development of a clinical demonstrator for computer assisted orthopedic surgery with CT-image based individual templates," Computer Assisted Radiology and Surgery, pp. 944-949, (1997) Elsevier Science B.V.
Radermacher, "Computer Assisted Orthopaedic Surgery with Image Based Individual Templates," Clinical Orthopaedics and Related Research No. 354, pp. 28-38 (Sep. 1998) Lippincott Williams & Wilkins.
Radermacher, K., et al., "Computer Integrated Orthopaedic Surgery: Connection of Planning and Execution in Surgical Intervention," Computer-integrated surgery: technology and clinical applications, (1996) pp. 451-463.
Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.
Radermacher, K., et al., "Image Guided Orthopedic Surgery Using Individual Templates," Springer Berlin/Heidelberg, CVRMed-MRCAS'97, vol. 1205/1997 pp. 606-615).
Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.
Radermacher, Klaus, et al. "Computer Assisted Orthopaedic Individual Templates." Clinical Orthopaedics and Related Research. (Sep. 1998) No. 354; pp. 28-38.
Schuller-Götzburg, P., et al., 3D-Implantatplanung und Stereolithographie-Implantatbohrschablonen, Stomatologie 101.3, pp. 55-59 (May 2004).
Sharp, S. Michael, Ph.D., Patient-Specific, Resurfacing Bi-Compartmental Arthuroplasty, Futuretech, Orthopaedic Product News (Mar./Apr. 2008) pp. 12-15.
Signature™ Hip Technology Personalized Patient Care brochure. Biomet® Orthopedics. (2013) (8 pages).
Signature™ Personalized Patient Care, Surgical Technique Addendum Vanguard® Complete Knee System, Biomet® Orthopedics Brochure, (2011), p. 1-32.

(56) References Cited

OTHER PUBLICATIONS

Signature™ Personalized Patient Care. Surgical Technique Acetabular Guide System brochure. Biomet® Orthopedics. (2013) pp. 1-13.

Sisto, Domenick, J., et al., "Custom Patellofemoral Arthroplasty of the Knee Surgical Technique," Journal of Bone and Joint Surgery, vol. 89-A, pp. 214-225 (Jul. 2006).

Slammin, John et al, "Do You Have This Implant in My Size?", MDT Medical Design Technology, 3 pages, http://www.mdtmag.com/scripts/ShowPR.asp?PUBCODE=046&ACCT=0007796&ISSUE . . . accessed Jul. 31, 2008.

Steinwachs, Matthias Reinhard, "Cartilage Repair—Autologous Chondrocyte Transplantation and Autologous Matrix-induced Chondrogenesis," European Musculoskeletal Review (2006) pp. 65-68.

Supplementary European Search Report dated Nov. 15, 2011 for EP07809326, which claims benefit of PCT/US2007/013223, filed Jun. 5, 2007; which claims benefit of U.S. Appl. No. 11/756,057, filed May 31, 2007.

Thomas, W., et al., "Endoprothetischen Versorgung des Kniegelenks auf der Basis eines 3D-computertomographischen Subtraktionversfahrens," Zuma Thema: Computergestützte orthopädische Chirugie, Der Orthopäde 29:641-644 Springer-Verlag (Jul. 2000) Translation provided: Thomas, W., "Endoprosthetic care of the knee joint based on a 3D computer chromatography subtraction process," Topic: Computer-aided orthopedic surgery. Orthopedist 2000 29:641-644 Springer Verlag (Jul. 2000).

What is Subchondroplasty, Retrieved from <http://www.subchondroplasty.com/about _subchondroplasty/what_is_ subchondroplasty. >, Jul. 1, 2013. 2 sheets.

\* cited by examiner

METHOD AND APPARATUS FOR A PIN APPARATUS

FIELD

The present teachings relate to an acetabular guide and particularly to a patient-specific guide and various associated instruments.

INTRODUCTION

The present teachings provide a patient-specific acetabular guide and associated instruments for implanting an acetabular implant into an acetabulum of a patient for hip joint arthroplasty.

SUMMARY

An acetabular guide system for placing a guide pin near an acetabulum, comprising: a patient specific acetabular guide including an interior surface and an exterior surface, the exterior surface being configured to have a geometry to register within the acetabulum of a specific patient; a first drill insert configured to be received by the patient specific acetabular guide at a first location, the first drill insert having a first longitudinal bore configured to be received concentrically in a guide bore of the patient specific acetabular guide, the guide bore extending exterior to the interior surface; a second drill insert configured to be fixed to a boney portion exterior to the acetabulum at a second location a predetermined distance from the first location, the second drill insert forming a second longitudinal bore; and a selectively removable alignment pin configured to be received by at least one of the first longitudinal bore and the second longitudinal bore.

The present teachings provide various instruments and methods for generally preparing the acetabulum of a patient to receive an acetabular implant, such as, for example, an acetabular cup along an alignment axis. The alignment axis, various patient-specific guides, and other associated instruments can be designed during a pre-operative plan using a three-dimensional reconstruction of the patient's relevant anatomy, such as the pelvis or portions thereof. The three-dimensional reconstruction can be based on medical images.

The present teachings provide, for example, a patient-specific acetabular guide that can be used for preparing an acetabulum of a patient to receive an acetabular implant, such as an acetabular cup. The acetabular guide has a dome-shaped body with a peripheral annular rim and an outer three-dimensional surface configured to match an acetabulum of a specific patient's hip joint from three-dimensional medical images of the patient's hip joint during a preoperative plan for the patient. A patient-specific registration guide can be permanently or removably attached to the peripheral rim. The patient-specific registration guide has a longitudinal bore defining a patient-specific alignment axis with an alignment orientation configured for guiding an acetabular implant for the patient during the preoperative plan of the patient. The registration guide has a patient-specific undersurface configured to mate with a corresponding portion of a periacetabular surface and/or acetabular rim surface of the acetabulum of the patient.

An acetabular guide system for placing a guide pin near an acetabulum, includes a patient specific acetabular guide including an interior surface and an exterior surface, the exterior surface being configured to have a geometry to register within the acetabulum of a specific patient, a first drill insert configured to be received by the guide at a first location, the first drill insert having a first longitudinal bore configured to be received concentrically in a guide bore of the guide, the guide bore extending exterior to the interior surface, a second drill insert configured to be fixed to a boney portion exterior to the acetabulum at a second location a predetermined distance from the first location, the second drill insert forming a second longitudinal bore, and a selectively removable alignment pin configured to be received by at least one of the first longitudinal bore and the second longitudinal bore.

In other features, a method of placing a guide pin near an acetabulum with an acetabular guide system includes providing a patient specific acetabular guide including forming an exterior surface of the patient specific acetabular guide to have a geometry to register within the acetabulum of a specific patient, providing a first drill insert having a first longitudinal bore configured to be received concentrically in a guide bore of the patient specific acetabular guide, the guide bore extending exterior to an interior surface of the patient specific acetabular guide to align the first drill insert at a first location, providing a second drill insert having a second longitudinal bore and configured to be fixed to a boney portion at a second location a predefined distance from the first location, and providing a selectively removable alignment pin configured to be received by at least one of the first longitudinal bore or the second longitudinal bore.

In yet other features, a method for implanting an acetabular implant includes forming a patient specific acetabular guide having an exterior surface with a geometry formed to register within an acetabulum of a specific patient, connecting a first drill insert to the patient specific acetabular guide at a first location relative to the acetabulum, the first drill insert having a first longitudinal bore configured to be received concentrically in a guide bore of the patient specific acetabular guide, the guide bore extending exterior to the interior surface to align the first drill insert at a first location, fixing an alignment pin to a first portion of bone at the first location, the alignment pin being received by the first longitudinal bore, removing the patient specific acetabular guide and the first drill insert, coupling a driver to the alignment pin, driving, using the driver, a second drill insert, having a second longitudinal bore, into a second portion of bone at a second location, the second location being at a predetermined distance from the first location, and selectively removing the alignment pin from the first drill insert Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The present teachings will become more fully understood from the detailed description and the accompanying drawings, wherein.

Corresponding reference numerals indicate corresponding parts throughout the several views of the drawings.

DETAILED DESCRIPTION

Figure 1A:
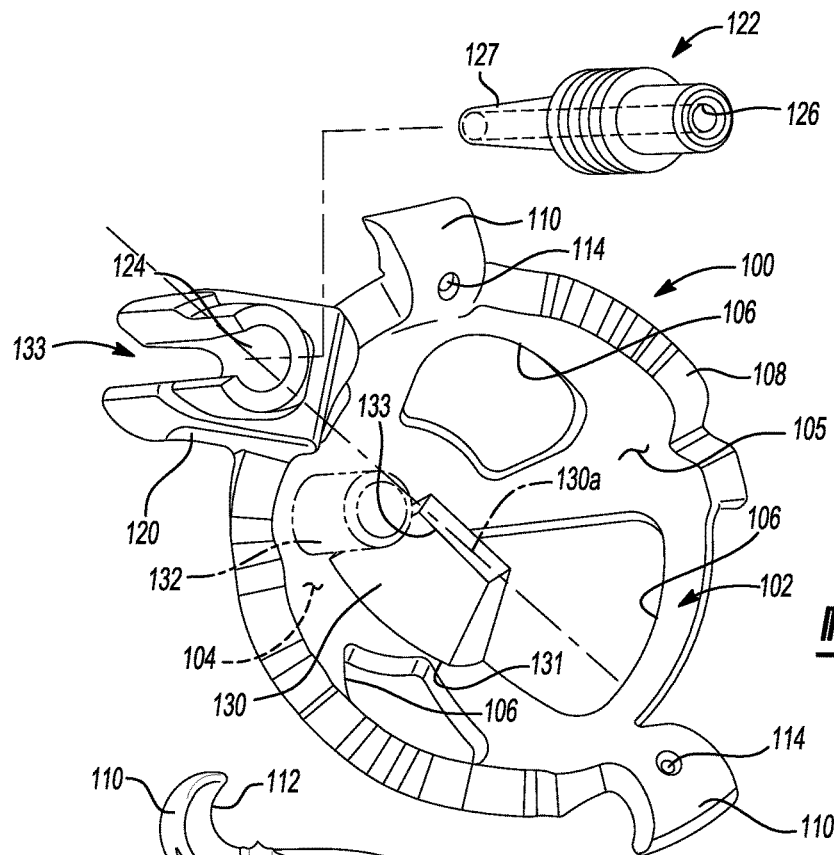
FIG. 1A is a front isometric view of a patient-specific acetabular guide according to the present teachings.
Figure 1B:
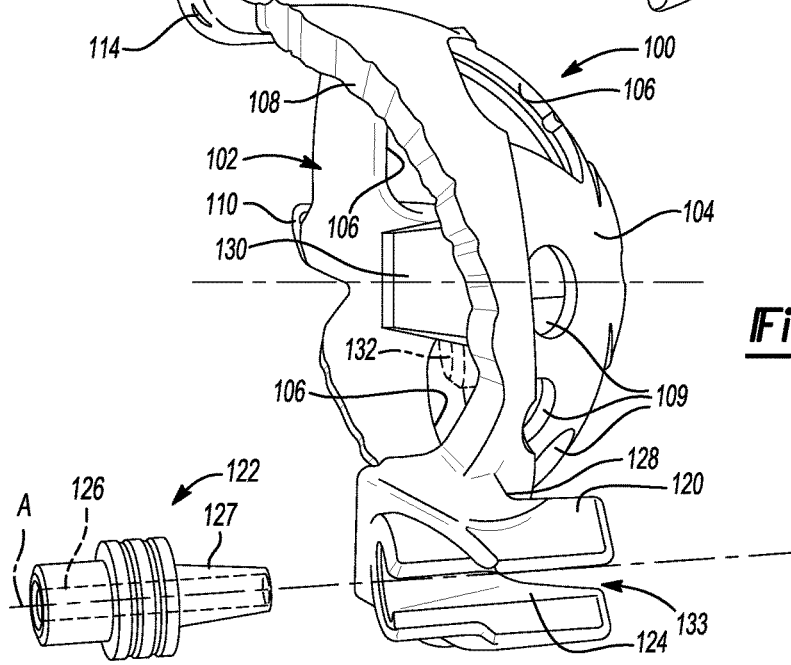
FIG. 1B is side isometric view of the patient-specific acetabular guide of FIG. 1A.

The following description is merely exemplary in nature and is in no way intended to limit the present teachings, applications, or uses.

The present teachings generally provide patient-specific acetabular alignment guides, inserters and/or other associated instruments for use in orthopedic surgery, such as, for example, in joint replacement or revision surgery for the hip. The patient-specific alignment guides and associated instruments can be used either with conventional or with patient-specific implant components prepared with computer-assisted imaging methods based on medical scan of the specific patient.

As described in U.S. Pat. No. 8,092,465, issued Jan. 1, 2012, and U.S. Patent Application Publication No. 2012/0226283, filed Feb. 21, 2012, 2014/0276873, filed Mar. 11, 2014, all of which are incorporated by reference herein, during a preoperative planning stage, imaging data of relevant anatomy of a patient may be obtained at a facility, including a doctor's office. The imaging data may include, for example, a detailed scan of a pelvis, hip, knee, ankle, or other joint or relevant portion of the patient's anatomy. The imaging data may be obtained using an MRI, CT, and X-Ray, ultrasound or any other imaging systems. The imaging data obtained may be used to construct a three-dimensional computer image of the joint or other portion of the anatomy of the patient and prepare an initial preoperative plan that may include bone or joint preparation, such as planning for resections, milling, reaming, broaching, as well as implant selection and fitting, design of patient-specific guides, templates, tools and alignment protocols for the surgical procedure. Additionally, physical modes of the patient's joint and associated bones may be prepared for visualization and trialing of the guides and implants prior to the surgical procedure.

Computer modeling for obtaining three-dimensional computer images of the relevant patient's anatomy may be provided by various computer aided drafting (CAD) programs, applications and/or software commercially available from various vendors or developers, such as, for example, from by Object Research Systems or ORS, Montreal, Canada. The computer modeling program or other application may be configured and used to plan a preoperative surgical plan, including planning various bone preparation procedures, to select or design/modify implants and design patient-specific guides and tools. The patient-specific guides and tools may include patient-specific prosthesis components, and patient-specific tools, including reaming, broaching, milling, drilling or cutting tools, alignment guides, templates and other patient-specific instruments.

The preoperative plan may be stored in any computer storage medium, in a computer file form or any other computer or digital representation, including three-dimensional graphical files or digital data sets. The preoperative plan, in a digital form associated with interactive software or other application, may be made available via a hard medium, a web-based or mobile or cloud service, or a portable device that may have access to a cellular network. The plan may be provided via the various systems or media to the surgeon or other medical practitioner, for review. Using the interactive software or application, the surgeon may review the plan, and manipulate the position of images of various implant components relative to an image of the anatomy. The surgeon may modify the plan and send it to the manufacturer with recommendations or changes. The interactive review process may be repeated until a final, approved plan, is sent to a manufacturing facility for preparing actual physical components. In various embodiments, physical and digital patient-specific bone models, guides, and instruments may be provided preoperatively to the surgeon for trialing and marking.

After the surgical plan is approved by the surgeon, patient-specific implants and associated tools, including, for example, alignment guides, cutting/milling/reaming/broaching or other tools for the surgical preparation of the joint or other anatomy portion of the specific patient may be designed using a CAD program or other three-dimensional modeling software, such as the software provided by Object Research Systems or ORS, Montreal, Canada, for example, according to the preoperative surgical plan. Patient-specific guides and other instruments may be manufactured by various stereolithography methods, selective laser sintering, fused deposition modeling, or other rapid prototyping methods, and/or computer controlled machining. In some embodiments, computer instructions of tool paths for machining the patient-specific guides and/or implants may be generated and stored in a tool path data file. The tool path data may be provided as input to a CNC mill or other automated machining system, and the tools and implants may be machined from polymer, ceramic, metal or other suitable material depending on the use, and sterilized. The sterilized tools and implants may be shipped to the surgeon or medical facility for use during the surgical procedure.

Patient-specific implants, guides, templates, tools or portions thereof are defined herein as those constructed by a preoperative plan for a specific patient from three-dimensional images of the specific patient's anatomy reconstructed from preoperative image scans of the patient. The patient-specific components are constructed to closely conform and mate or match substantially to a surface of the patient's anatomy. The mating or matching is generally as a negative mold, negative surface, or inverse or mirror surface of corresponding surface portions of the patient's anatomy. The anatomical surfaces may include bone surfaces with or without associated soft tissue, such as articular cartilage, depending on the particular procedure, implant and tool use.

Minute irregularities, such as those that would not affect placement of the guide, of the patient's joint surfaces need not be mirrored.

As discussed above, patient-specific alignment guides and implants are generally configured to match the anatomy of a specific patient and fit/register to the patient in only one position on a corresponding surface of the specific patient because anatomic features that are unique to each patient may function as landmarks and may guide placement of the alignment guide or implant in only one position without the need of intraoperative image navigation, patient marking, or other intraoperative guidance. The patient-specific alignment guides are generally configured and manufactured using computer modeling based on the 3-D anatomic image of the patient and have an engagement surface that is made to conformingly contact and match, as discussed above, to a corresponding surface of a three-dimensional image/model of the patient's bone surface (with or without cartilage or other soft tissue), by the computer methods discussed above.

Generally, the patient specific guide has an exterior surface that directly contacts a selected portion of a selected region of a specific patient's anatomy. For example, a patient specific guide can include an exterior surface (e.g. an external dome surface of an acetabular guide) that directly contacts about 80% of the patient's anatomy (e.g. a specific patient's acetabulum) when properly positioned, including about 90% contact, and about 98% contact. The exterior surface of the patient matched guide may, therefore, substantially mate with the selected portion of the anatomy. It is understood, however, that certain exterior portions of a patient specific guide may not have substantial contact with the patient, while other portions are designed to ensure contact even when other portions are not contacting the patient. Thus, a patient matched guide may have portions that are substantially patient matched and have or may achieve the selected amount of contact with the patient.

The patient-specific alignment guides may include one or more custom-made guiding formations, such as, for example, guiding bores or cannulated guiding posts or cannulated guiding extensions or receptacles that may be used for supporting or guiding other instruments, such as drill guides, reamers, cutters, cutting guides and cutting blocks or for inserting pins or other fasteners according to a surgeon-approved pre-operative plan. The patient-specific alignment guides may be used in minimally invasive surgery, and also in surgery with multiple minimally-invasive incisions. Various alignment guides and pre-operative planning procedures are disclosed in U.S. Pat. No. 8,092,465, issued Jan. 10, 2012; U.S. Pat. No. 8,070,752, issued Dec. 6, 2011; U.S. Pat. No. 8,133,234, issued Mar. 13, 2012; U.S. Publication No. 2009/0024131, published Jan. 22, 2009; U.S. Publication No. 2008/0114370 dated May 15, 2008, now U.S. Pat. No. 8,298,237, issued Oct. 30, 2012; U.S. Publication No. 2011/0224674, published Nov. 15, 2011; U.S. Publication No. 2011/0184419, published Jul. 28, 2011; and U.S. Publication No. 2012/0226283, published Sep. 6, 2012, all patents and applications are incorporated herein by reference.

Referring to FIGS. 1A-3B, the present teachings provide a patient-specific acetabular guide 100 and an acetabular guide inserter 300. The acetabular guide 100 can be used in connection with various other instruments to generally provide a patient-specific alignment axis A. The patient-specific alignment axis A is used to insert an alignment pin 230 and generally to orient, insert, and implant an acetabular implant or acetabular cup 250 in an acetabulum (or acetabulum cavity) 82 of the patient, to facilitate guided reaming of the acetabulum 82, and generally guide any instruments and procedures relative to the alignment axis A or the alignment pin 230. The alignment axis A is determined during the preoperative plan from the three-dimensional image of the hip joint of the patient as the axis along which the acetabular implant 250 is to be inserted. The alignment axis A is generally perpendicular to the acetabulum 82 and corresponding acetabular engagement surface 252 of the acetabular implant 250. More specifically, with reference to FIG. 3B, the orientation (i.e., angles) of the alignment axis A can be selected and specified relative the axial plane (AP), sagittal plane (SP) and anterior pelvic plane (APP) of the pelvis 80. The coronal plane is a vertical plane that is orthogonal to the axial and sagittal planes (not shown). The anterior pelvic plane (APP) is defined as a plane passing through the two anterior iliac spines and the pubic symphysis of the pelvis 80 of the patient. The APP may deviate from being parallel to the coronal plane when viewed in the weight-bearing profile of the patient (standing). Additionally, the APP plane may have a different orientation in the supine position. The deviation varies from patient to patient, such that the anterior pelvic plane cannot be relied on by the surgeon without additional information to guide the acetabular implant and avoid impingement during motion. The angle between the anterior pelvic plane and the coronal plane can be referenced as a pelvic tilt and is zero when the anterior pelvic plane is parallel to the coronal plane. The present teachings determine a patient-specific axis for inserting an acetabular implant. The patient-specific alignment axis is physically and uniquely identified by the orientation of an alignment pin 230 inserted into the bone using the patient-specific acetabular guide and landmark registration incorporated into the acetabular guide during the preoperative plan. Specifically, the preoperative plan that is based on images of the hip joint of the patient can accurately determine the orientation of the alignment axis A and fix it intraoperatively via the patient-specific acetabular guide 100 on the pelvis 80 of the patient to guide the surgeon during the surgical procedure.

Figure 4:
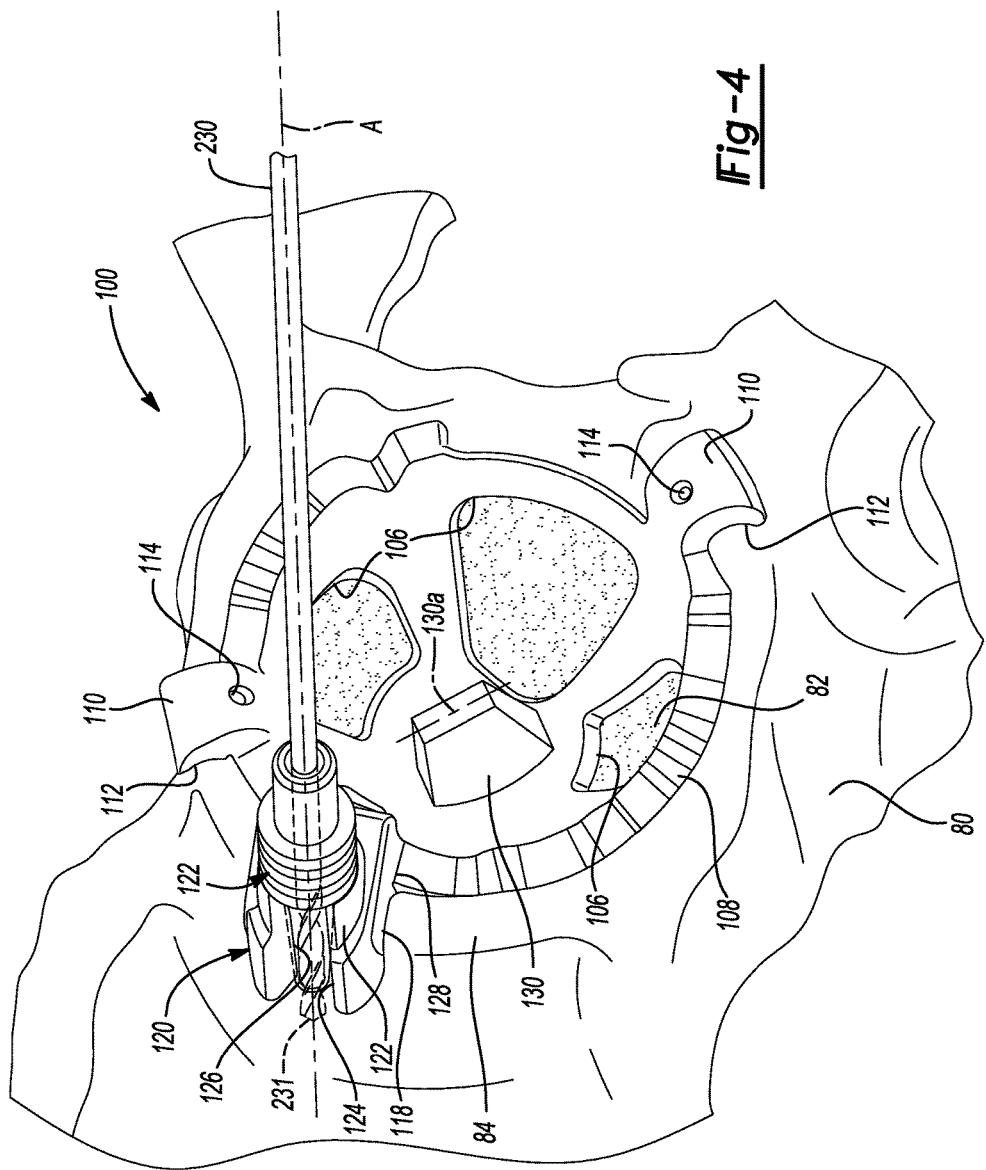
FIG. 4 is another isometric environmental view of the patient-specific acetabular guide of FIG. 1 and an alignment pin.

The patient-specific acetabular guide 100 can engage and register to the acetabulum 82 of the specific patient in a unique (only one) position and can provide an accurate alignment axis A relative to the planned orientation of an acetabular implant 250 (FIG. 4). The patient-specific acetabular guide 100 can also provide secure fitting and rotational stability in a design that is lightweight and has compact size and small bulk.

FIGS. 1A-3B illustrate a patient-specific acetabular guide 100 that has a dome-shaped body 102 with a three dimensional patient-specific undersurface or outer surface 104 configured to contact and engage the acetabulum 82. The outer surface 104 is designed and/or formed to match as a negative of a corresponding surface of the acetabulum 82 from the three-dimensional image of the patient's hip joint. Thus, the outer surface 104 is formed to mate closely, such as to contact about 85% to about 100% of the acetabulum 82 when positioned in the acetabulum 82. Thus, the outer surface 104 of the guide 100 includes a surface that may mirror or match the acetabulum 82.

The dome-shaped body 102 of the patient-specific acetabular guide 100 can have one or more openings in the form of windows 106 that reduce the weight of the patient-specific acetabular guide 100 and provide improved visualization of the underlying anatomy. The dome-shaped body 102 can also include additional holes or other apertures 109 for drilling holes in the acetabulum 82 and corresponding to holes 254 for fixation screws of the acetabular implant 250.

The dome-shaped body 102 of the patient-specific acetabular guide 100 is bounded by a guide rim 108 in the form of a closed-contour peripheral annular surface that may have uneven, irregular, jagged or wavy shape that follows a corresponding shape of an acetabular rim 84 (and periacetabular surface) around the acetabulum 82 of the patient.

Additionally, the patient-specific acetabular guide 100 can include one or more registration hooks, which may also be referred to as extensions or flanges, 110 that extend from the guide rim 108 along a three-dimensional curved surface around the acetabular rim 84 at different and spaced-apart positions. The registration hooks 110 are configured to provide additional registration locations for the patient-specific acetabular guide 100 by replicating corresponding underlying surface portions or landmarks of the acetabular rim 84 in a patient-specific manner. Specifically, each registration hook 110 can have a curved (three-dimensional) undersurface 112 that is patient-specific and negative of the surface of the acetabular rim 84 at specific locations selected as landmark locations during the preoperative plan for the patient. Each registration hook 110 can include a hole 114 for receiving a fixation pin or other fixation element (not shown) for attaching the patient-specific acetabular guide 100 to the pelvis of the patient. In addition, the registration hooks 110 may include a reinforcing ridge or rib. Selected reinforcing ribs include those illustrated and described in U.S. patent application Ser. No. 13/790,770, filed on Mar. 8, 2013, incorporated herein by reference.

The patient-specific acetabular guide 100 can include a removable or non-removable registration and alignment guide 120 (referenced as registration guide 120, for short) that has a longitudinal bore 124 along the patient-specific alignment orientation A. A removable drill insert 122 with a longitudinal bore 126 that can be received concentrically in the bore 124 of the registration guide 120. The wall of the bore 124 of the registration guide 120 can define a taper that engages a complementary taper 127 of an end of the removable drill insert 122. The complementary tapers can ensure appropriate and selected alignment of the bore 124 and the insert bore 126. Thus, the bore 124 and the insert bore 126 can be concentric and coextensive.

The drill insert 122 can provide stability and wear resistance during the insertion of an alignment pin 230. The alignment pin 230 can be inserted along the alignment axis A and further have a longitudinal axis that then extends along the alignment axis A. The alignment pin 230 can include a drill tip 231 that can drill into the bone of or near the acetabulum 82. The alignment pin 230 is received into the concentric bores 124, 126 of the registration guide 120 and the drill insert 122. Accordingly, the alignment pin 230 is oriented along the alignment axis A.

The drill insert 122 can be formed of a tough and/or strong material. For example, the drill insert 122 can be metallic and reusable, while the registration guide 120 and the acetabular guide 100 are patient-specific and can be made of a softer material, such as a polymer material, and can be disposable. The tough material of the drill insert 122 can engage the alignment pin 230 without deformation and/or wear to protect the registration guide 120 from damage due to engaging the alignment pin 230. Further, during insertion of the pin 230, the drill insert 122 is generally formed to not wear enough to allow movement of the pin 230 from the alignment axis A.

Figure 1C:
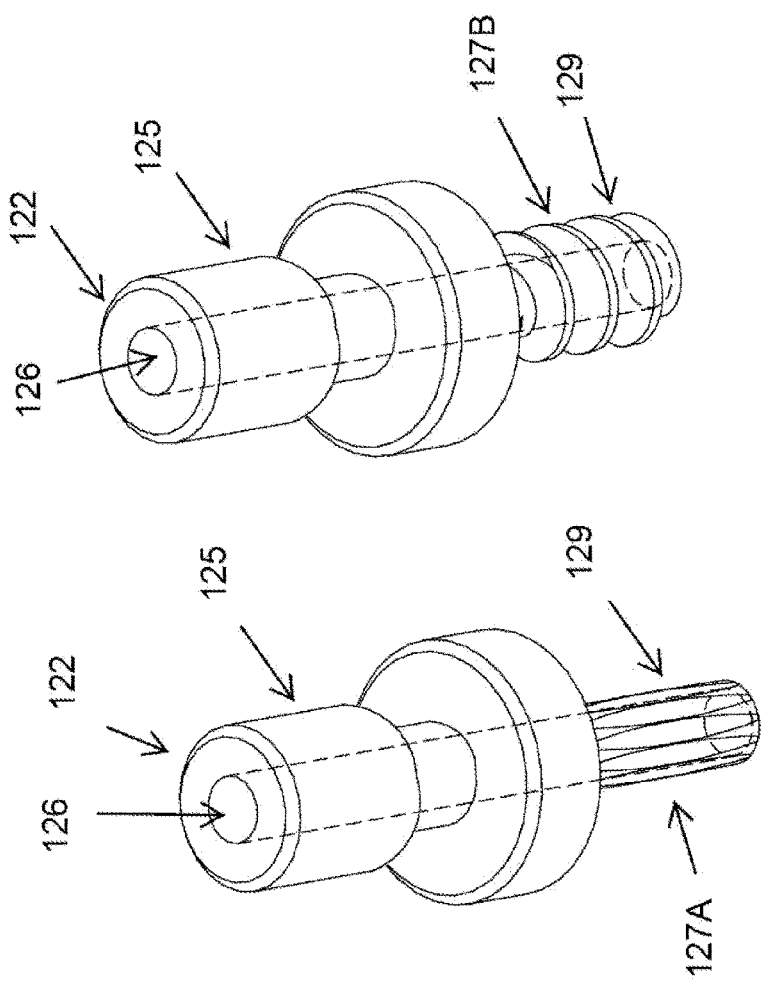
FIG. 1C is a perspective view of alternative drill inserts according to the present teachings.

In some embodiments, the drill insert 122 includes a proximal portion 125 and a distal portion 129. The distal portion 129 may include one of a plurality of bone engaging fins 127a and a plurality of threads, such as self-taping threads, 127b as illustrated in FIG. 1C. It is understood that while only fins and threads are described herein, the drill insert 122 may include any suitable fixation and/or anti-withdrawal feature. Each of the fins 127a and threads 127b are configured to be drilled into the bone at or near the acetabulum 82 and resist withdrawal of the drill insert 122 from the bone. It is understood, however, that multiple drill inserts or pin guides may be provided. Those with the fin 127a or the thread 127b may not directly engage the guide 100, as discussed herein.

Figure 7:
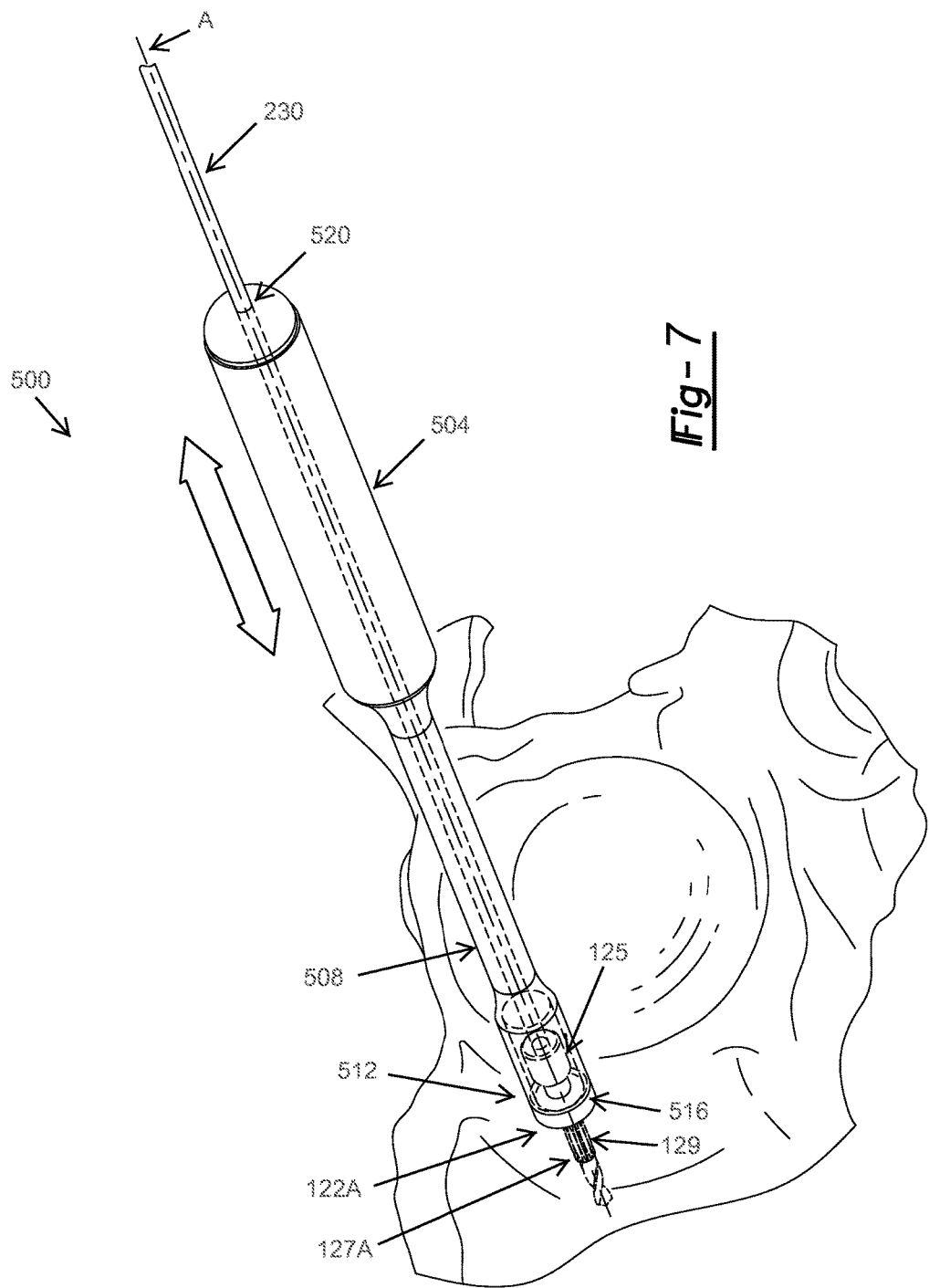
FIG. 7 is an isometric environment view of acetabulum and tool and the alternative drill insert and alignment pin of FIGS. 6A-6B
Figure 8:
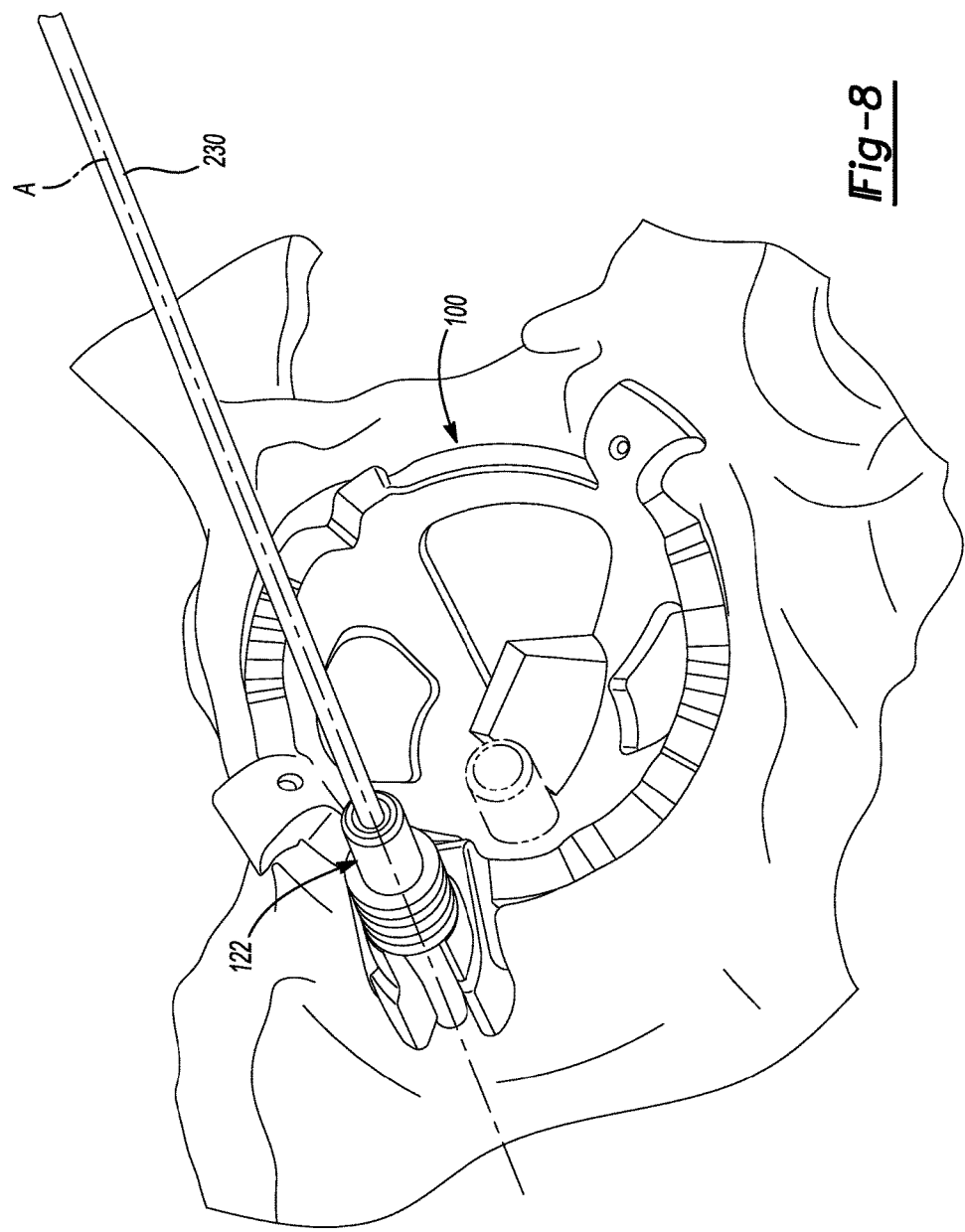
FIG. 8 is an isometric environment view of the patient-specific acetabular guide of FIG. 1 including a drill insert.

Briefly turning reference to FIGS. 7 and 8, a tool, such as a driver 500 includes a handle 504, a shaft 508, and a socket portion 512. The socket portion 512 is configured to engage the proximal portion 125 of the drill insert 122. For example, the socket portion 512 includes a distal opening 516. The distal opening 516 is configured to receive the proximal portion 125 of the drill insert 122, such as within an interior wall of the socket portion 512. The interior wall may form a hexagonal engagement, or other appropriate engagement.

As will be described below, the socket portion 512 may engage the proximal portion and drive or move the insert 122 along the axis A, such as with the handle 504. As the engaging portion engages the proximal portion 125, the drill insert 122 is pushed, causing the fins 127a to engage the bone and drive the distal portion 129 into the bone. It is understood that while drill insert 122 is shown with the fins 127a, the principles herein apply to a drill insert that includes the threads 127b, or any suitable anti-withdrawal feature.

The shaft 508 is configured to provide a sufficient length between the handle 504 and the socket portion 512. For example, the shaft 508 may provide a length long enough for a surgeon to operate the driver 500 without having to enter a patient's anatomy. It is understood the shaft 508 may be of any suitable length.

The handle 504 is configured to receive a surgeons hand for operation of the driver 500. In use, the surgeon may rotate the handle relative to the axis A, thereby causing the socketed portion 512 to engage the proximal portion 125 and drive the distal portion 129 into the bone, as described above. Also, a hammer or other tool may be used to impact or turn the driver 500.

As illustrated in FIG. 7, the driver 500 includes a through bore 520. The through bore 520 passes concentrically through the handle 504, the shaft 508, and the socket portion 512. Further, the through bore 520 may be concentric and coextensive with the insert bore 126 of the drill insert 122 when engaging the drill insert 122. In this manner, the alignment pin 230 may pass through the driver 500 and through the drill insert 122. After the surgeon drills the drill insert 122 into the bone, the driver 500 may be removed along the axis A, leaving the alignment pin 230 assembled in the drill insert 122.

FIG. 8 illustrates an alignment pin 230 assembled in a drill insert 122. In some implementations, the drill insert 122 may include the fins 127a or the threads 127b disposed on the distal portion 129 of the drill insert 122 as described with respect to FIG. 1C. The fins 127a may be received concentrically in the bore 124 of the registration guide 120. Thus, any other suitable anti-withdrawal feature, or no anti-withdrawal feature as illustrated in FIG. 8, may be used with the guide 100.

The registration guide 120 may have an undersurface portion that is a patient-specific undersurface 128 that can hook around or snap-on or otherwise engage and contact the guide rim 108 at a pre-defined marked location determined during the preoperative plan of the patient. The registration guide 120 that includes the patient-specific undersurface 128 matches the surface of the acetabular rim 84 and/or periacetabular area of the pelvis 80 of the patient at a corresponding location.

The bore 124 of the registration guide 120 and the bore 126 of the drill insert 122 can have an open (i.e., non-continuous) periphery defining a longitudinal slit 133. The slit 133 may be configured to allow the patient-specific acetabular guide 100 to be removed from the pelvis 80 of the patient without removing the alignment pin 230 that is inserted into the pelvis 80 and defines the alignment axis A. In other words, the patient-specific acetabular guide 100 can be also removed by side or lateral motion relative to the slit 133 and the longitudinal axis A and not necessarily by only motion along the alignment axis A or along the alignment pin 230.

The patient-specific acetabular guide 100 can include a first post 130 and, optionally, a second post 132 (shown in phantom). Both of the posts 130, 132 may extend from an interior surface 105 (opposite to outer surface 104) of the dome-shaped body 102 of the patient-specific acetabular guide 100. The post 130, as discussed herein, assists with placement and alignment of the guide 100. Further, it is understood that the second post 132 is optional and need not be included with the guide 100.

The first post 130 may, optionally, define a bore that passes through the dome-shaped body 102 of the acetabular guide for optional fixation to the acetabulum 82 using a pin or other fastener. The bore is not necessary, however, and the post 130 can be a closed hollow post or a solid post. The first post 130 can be centrally located and perpendicular relative to a tangent to the dome-shaped body 102 of the patient-specific acetabular guide 100 and the underlying surface of the acetabulum 82. The optional second post 132, if included, can be offset relative to the first post 130 in a radial direction relative to the periphery of the guide rim 108. The second post 132 can be shorter in height relative to the first post 130. The posts 130, 132 can be used to insert the patient-specific acetabular guide 100 using an acetabular guide inserter, such as the acetabular guide inserter 300 shown in FIG. 2-3B.

The post 130 can be an insertion and alignment post that extends from and is formed with the guide 100. It is further understood, however, that the insertion post 130 can be interconnected with the guide 100 in any appropriate manner, such as with an adhesive or other fixation mechanism. Regardless, the post 130 may be formed to include a non-circular or non-cylindrical shape. For example, the post 130 can include a trapezoidal, oval, oblong or other selected shape. The non-circular shape can be viewed in cross-section of the post 130 and/or along an axis extending along a height of the post 130.

The post 130 can include a post alignment axis 130a that can have a specific orientation relative to the guide 100, and particularly to the alignment axis A through the registration guide 120. The post alignment axis 130a may be used to align the guide 100 relative to a selected portion of the anatomy, including an anatomical landmark, as discussed further herein. The anatomical landmark can be predetermined in the patient image, such as during planning the procedure. Accordingly, the post 130, including a post alignment axis 130a can assist in rotationally aligning the guide 100 relative to the acetabulum 82 in the pelvis 80. Moreover, the non-circular shape of the post 130 can assist in holding and engaging the guide 100 relative to a selected insertion instrument 300 (FIGS. 2A and 2B), as discussed further herein. Moreover, the post 130 can include an external geometry that tapers towards a base 131 of the post 130 near the internal surface 105 of the guide 100. Again, the taper of the post 130 can assist in engagement and fixation of the guide relative to the insertion instrument 300, as discussed further herein.

Figure 2A:
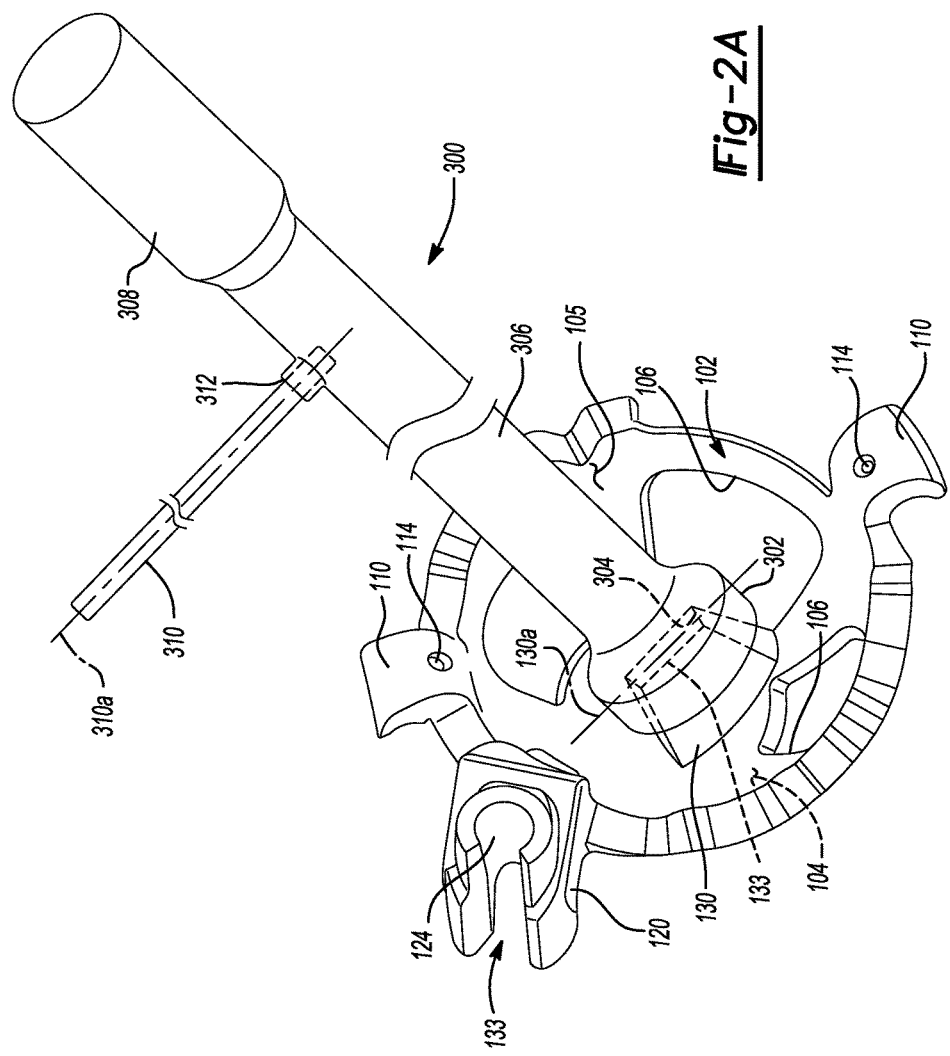
FIG. 2A is top isometric view of the patient-specific acetabular guide with an insertion handle, according to the present teachings.
Figure 2B:
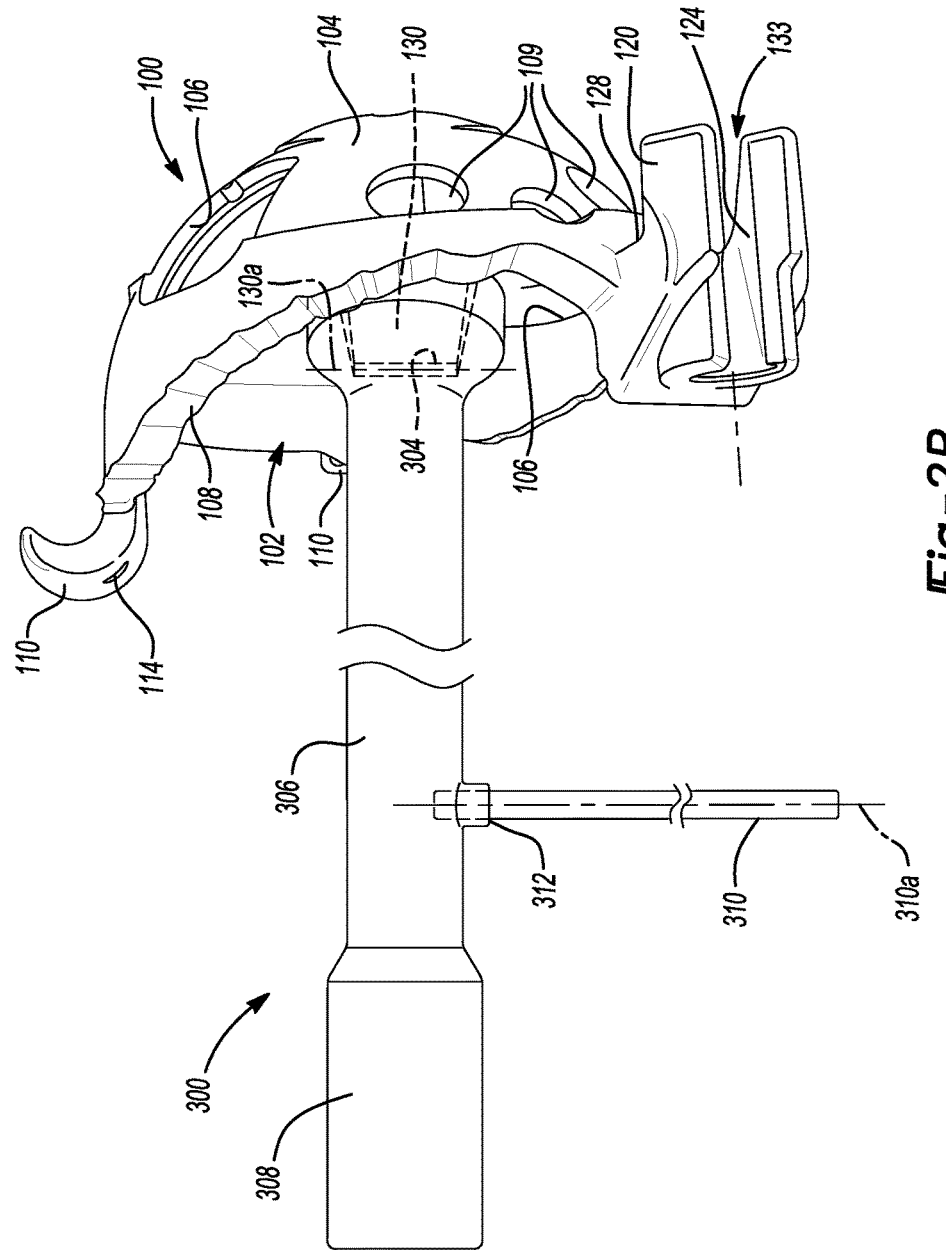
FIG. 2B is side plan view of the patient-specific acetabular guide with an insertion handle, according to the present teachings.

With particular reference to FIGS. 2A and 2B, the inserter 300 can engage the first post 130 near a first end 302 that defines an internal bore or capture area 304 that is complementarily shaped and/or mates with an upper or top portion 133 of the post 130. As discussed above, the shape of the central post 130 can define the post alignment axis 130a. The complimentary internal bore 304 of the inserter instrument 300 can also define an inserter bore axis that mates or aligns with the post alignment axis 130a once the inserter 300 engages the post 130. Accordingly, the instrument 300 engages and may couple to the post 130 in a selected and keyed manner. In the keyed manner the inserter 300 engages the post 130 in a selected single orientation and position, which also allows the inserter 300 to be positioned at a single orientation and position relative to the guide 100. The inserter 300, therefore, can be interconnected with the guide 100 and a selected single orientation and position to allow for manipulating the guide relative to the pelvis 80.

The first end 302 of the shaft 306 can further include a taper that engages the external taper of the post 130. A female taper of the receiving bore 304 coupling with the external taper of the post 130 can assist in holding and fixing the post 130, and the guide 100, relative to the inserter handle 300. It is understood, however, that additional attachment mechanisms can also be provided such as an interference fit, a snap fit, a screw or bolt that engages the post 130 relative to the handle 300, or other appropriate connection mechanisms.

Additionally, the inserter 300 can include a shaft 306 that extends to a handle 308. The handle 308 can be grasped by a user to manipulate the inserter 300 relative to the guide 100 for engaging the post 130. Once the inserter 300 is coupled to the post 130 the inserter can then further translate and rotate the guide 100 relative to the pelvis 80 once the handle 300 is engaged on the post 130.

Additionally, the inserter 300 can include an alignment portion, such, as a jig or alignment rod 310, which may be coupled to and/or formed with the shaft 306 at an engagement or coupling region 312. The alignment portion can be viewed exterior to soft tissue of the patient by a user during insertion and positioning the guide 100 from. Thus, the user can know an alignment of the guide 100 by viewing the alignment portion as the inserter 300 engages the post 130 in a single location and orientation.

The coupling region 312 can include an internal thread to engage an external thread of the alignment jig or rod 310. Additionally, however, further connection mechanisms can be provided such as a slotted aperture which allows the alignment jig or rod to directly contact a pre-defined portion of anatomy or soft tissue. Alternatively, the alignment portion, such as the alignment jig 310, may be permanently fixed or manufactured with the shaft 306 as a single piece. Nevertheless, the alignment jig 310 can extend from the shaft 306 along an alignment portion or jig axis 310a. The alignment portion axis 310a of the alignment jig 310 can be formed to align with the post alignment axis 130a of the post 130. Because the post 130 engages the internal bore 304 in the shaft 306 in a single selected and predetermined location and orientation, the shaft 306 will engage and align with the post 130 in a substantially single orientation and position. Thus, the alignment jig 310, which defines the alignment axis 310a, is aligned with the axis 130a of the post 130. It is understood, however, that the alignment jig 310 is not required and that the handle 300 engaging the post 130 can provide appropriate fixation and alignment for a user, for purposes as discussed further herein.

Figure 3A:
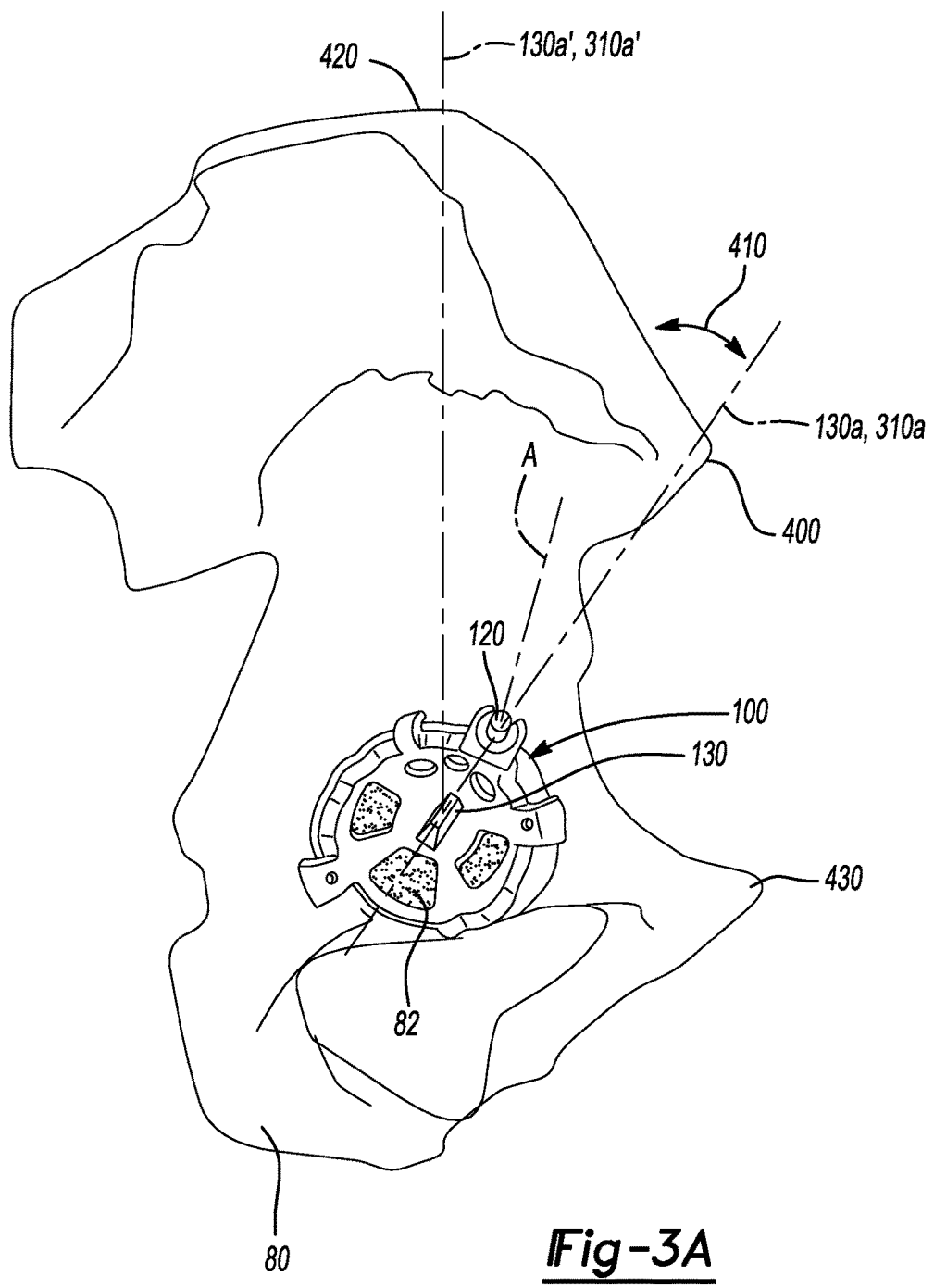
FIG. 3A is an isometric environmental view of the patient-specific acetabular guide of FIG. 1.
Figure 3B:
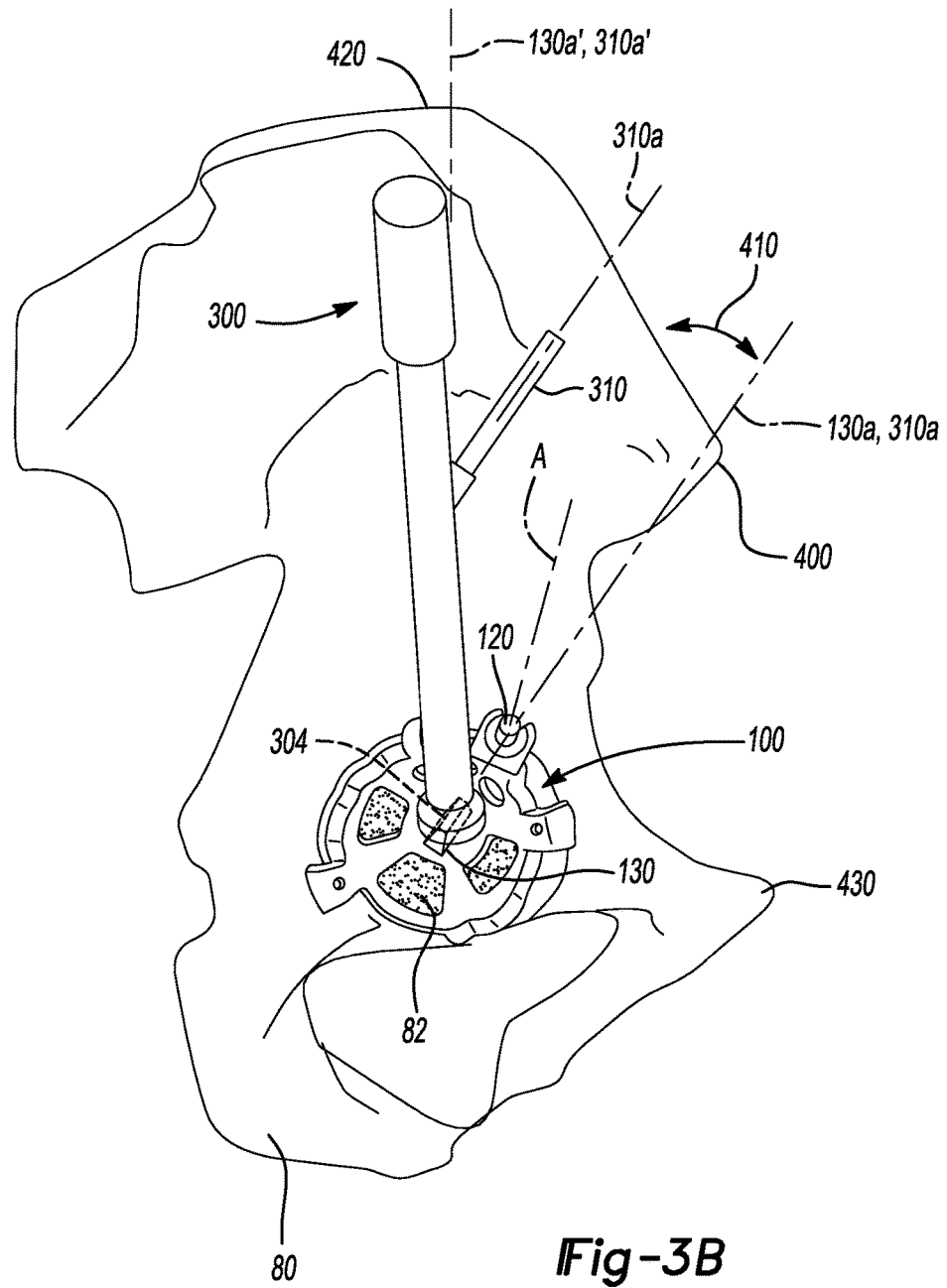
FIG. 3B is an isometric environmental view of the patient-specific acetabular guide of FIG. 1 with an inserter attached.

With reference to FIGS. 3A and 3B, the guide 100 can be positioned in the acetabulum 82 of the pelvis 80 in a selected manner. As discussed above, the central post 130 defines the post alignment axis 130a. As the inserter 300 is aligned with the axis 130a, due to the engagement of the bore 304 with the post 130, the handle 300 can be visually viewed from exterior to the patient. Additionally, the alignment jig 310 can also be positioned on a portion of the shaft 306 such that it is also exterior to the patient when the guide 100 is positioned near or within the acetabulum 82. It is understood, that when viewed from an exterior of the patient, a user, such as a surgeon, can have a clear view of the alignment jig 310 and/or a portion of the inserter 300 while positioning the guide 100 within the acetabulum 82.

The post alignment axis 130a can be extended exterior to the guide 100 to allow for alignment with a portion of the pelvis, such as an anatomical landmark 400, which can include the Anterior Superior Iliac Spine (ASIS), due to positioning of the guide 100 within the acetabulum 82. The anatomical landmark can be predetermined, such as during planning of the procedure. The alignment axis A through the registration guide 120 can also be selected during a pre-planning process. The design of the guide 100 can then be based on the predetermined landmark and the predetermined location of the alignment axis A. The guide 100 can then be manufactured to have the post 130 with the post alignment axis 130a formed relative to the alignment axis A such that alignment of the post alignment axis 130a with the predetermined landmark will place the alignment axis A at the predetermined location and orientation.

Accordingly, the position of axis A relative to the acetabulum 82 can be pre-determined and can be positioned relative to the pelvis 80 due to registration of the guide 100 within the acetabulum 82. As discussed above, the guide 100 registers within the acetabulum 82 (i.e., by substantial matching or contact of the exterior surface 104 of the guide 100 with the acetabulum 82) in substantially only a single location and orientation. Accordingly, the handle 300 can be used to position and rotate the guide 100 in the direction of Arrow 410. The inserter 300 can be used to sweep an arc of a selected length in either or both directions of arrow 410. The alignment jig 310 that defines the jig axis 310a that is aligned with the post alignment axis 130a can all be designed to ensure that registration of the guide 100 occurs when the alignment axis A is at the selected pre-planned position within the patient. Accordingly, via moving the handle 300, illustrated in FIGS. 2A and 2B, the surgeon can clearly view the alignment jig 310 relative to various landmarks of the patient, such as the ASIS 400, such as from exterior to soft tissue of the patient.

Rotating the guide 100 can move the post alignment axis 130a of the central post 130 relative to the pelvis 80. For example, as illustrated in FIG. 3B, the post alignment axis 130a of the post 130 can be positioned to point toward or be aligned with an iliac crest 420 of the pelvis 80. Positioning of the post alignment axis 130a' of the central post 130 aligns the jig axis 310A' of the jig 320 with the iliac crest 420 as well. During the procedure, the surgeon can view that the alignment jig 310 is oriented or aligned with the iliac crest 420 and determine that the guide 100 must be rotated anteriorly or towards a pubis 430. The user can then rotate the inserter 300 and the guide 100 as needed, and generally in the direction of one of the arrowheads 410. Thus, the user can determine an appropriate movement of the guide 100 to position the guide 100 relative to a pre-selected landmark, such as the ASIS 400. The alignment jig 310 can assist and/or ensure that the guide 100 is positioned and registered to the acetabulum 82 by allowing the user to view the jig 310, or selected portion of the inserter 300. Again, this assists in rotational alignment of the guide 100 at least because the inserter 300 engages the post 130 in the keyed manner. Accordingly, while the acetabular guide 100 will register within the acetabulum 82 at a selected single location and orientation, the alignment jig 310, viewed by the user, can assist in ensuring that the guide 100 is at a pre-selected or pre-planned location and increase the speed of aligning the guide 100 relative to the pre-planned and selected orientation.

It is understood that the guide 100 can be oriented relative to any selected anatomical landmark that can be viewed and/or palpated by a user during the procedure. For example, it is understood that the central post 130 can be designed and positioned within the guide 100 such that the post alignment axis 130a is aligned with the iliac crest 420 when the guide 100 is properly registered within the acetabulum 82. Accordingly, aligning the post alignment axis 130a with the ASIS 400 is not required for ensuring that the guide 100 is properly registered with the patient, if a pre-planned or pre-determined orientation of the guide 100 is selected as such that the axis 130A is to be aligned with a different landmark.

Nevertheless, based upon the pre-planned or pre-determined alignment with the selected landmark, the inserter 300 can be used to rotate the guide 100 relative to the acetabulum 82 during insertion and placement of the guide 100 within the acetabulum 82. Once appropriately registered, the inserter 300 can be removed from the central post 130 and the alignment pin 230 can be passed through the drill insert 122 that has been positioned within the registration guide 120, as illustrated in FIG. 4. The alignment pin 230, when inserted through the drill insert 122 that is positioned within the registration guide 120 generally extends along the alignment axis A that is pre-planned relative to the guide 100. Again, by positioning the guide 100 registered within the acetabulum 82 the alignment axis A is at the pre-planned and selected position relative to the acetabulum 82. Positioning of the alignment pin 230 through the drill insert 122 that is positioned within the registration guide 120 and drilling it into the pelvis 80 positions the alignment pin 230 along the axis A.

The positioning of the guide 100, as discussed above, is assisted by positioning the inserter 300 relative to the central post 130 to align the alignment jig 310, or other selected portion of the handle 300, along post alignment axis 130a of the central post 130. The guide 100, therefore, could be properly registered relative to the patient by aligning the alignment jig 300 relative to a selected anatomical landmark, such as the ASIS 400, at least via rotation of the handle 300 and the guide 100, due to coupling with the handle 300. In this way, the inserter 300 may be used to rotationally position the guide 100 for placement of the alignment axis A at the predetermined location and orientation for placement of the pin 230.

Figure 5:
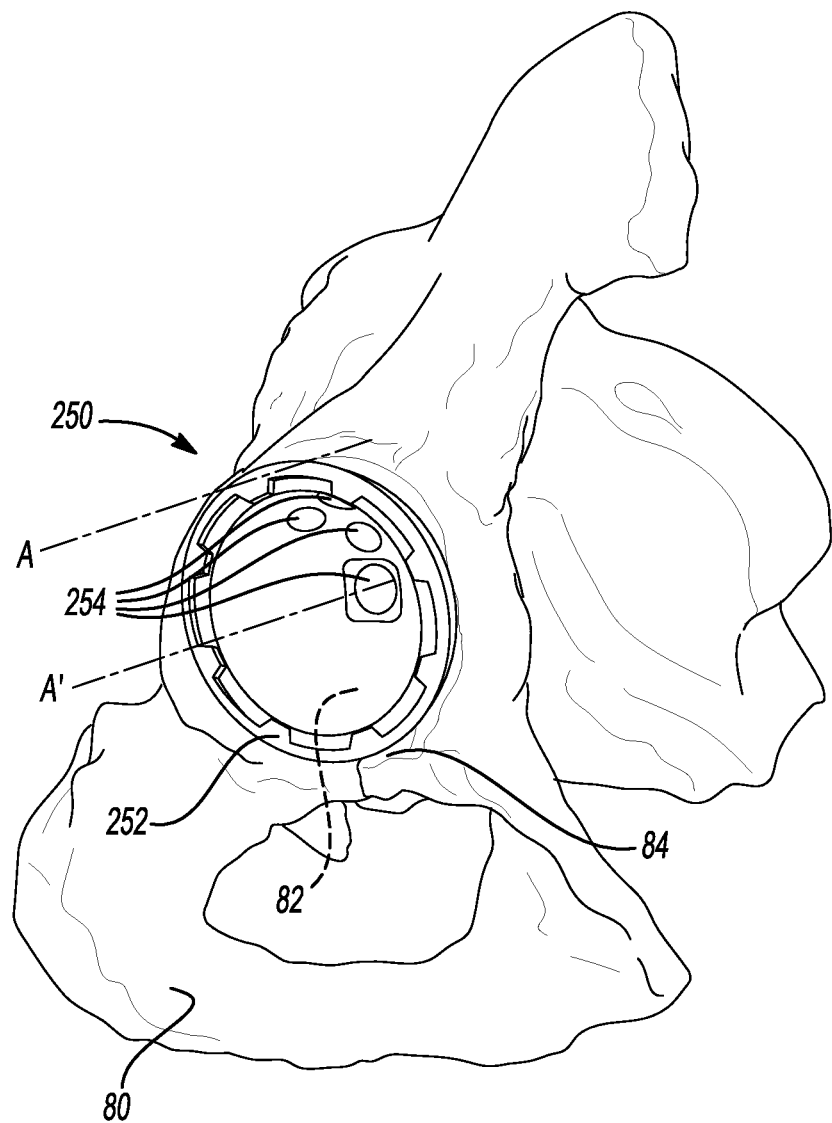
FIG. 5 is an isometric environmental view of an acetabular implant.
Figure 6A:
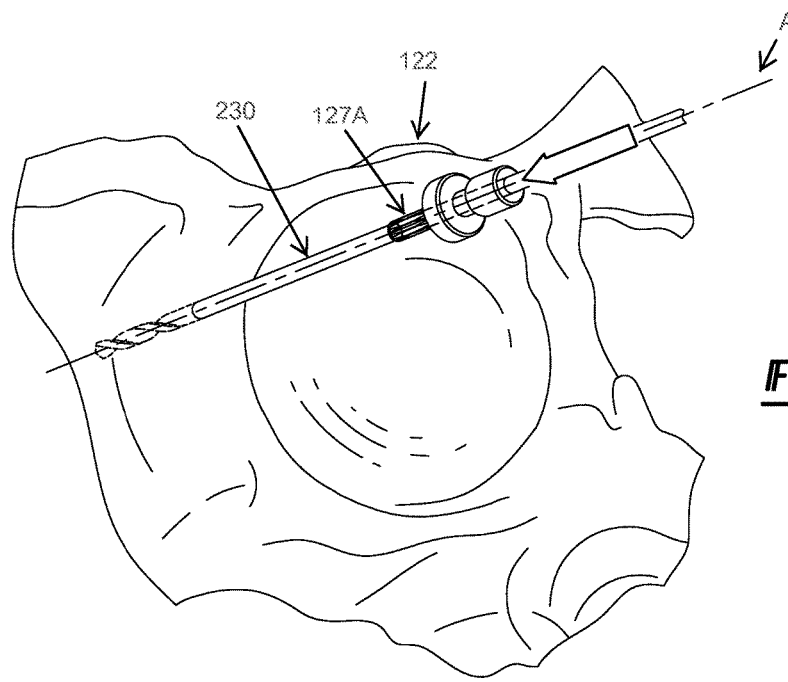
FIGS. 6A-6B are an isometric environmental view of acetabulum and an alternative drill insert and alignment pin.
Figure 6B:
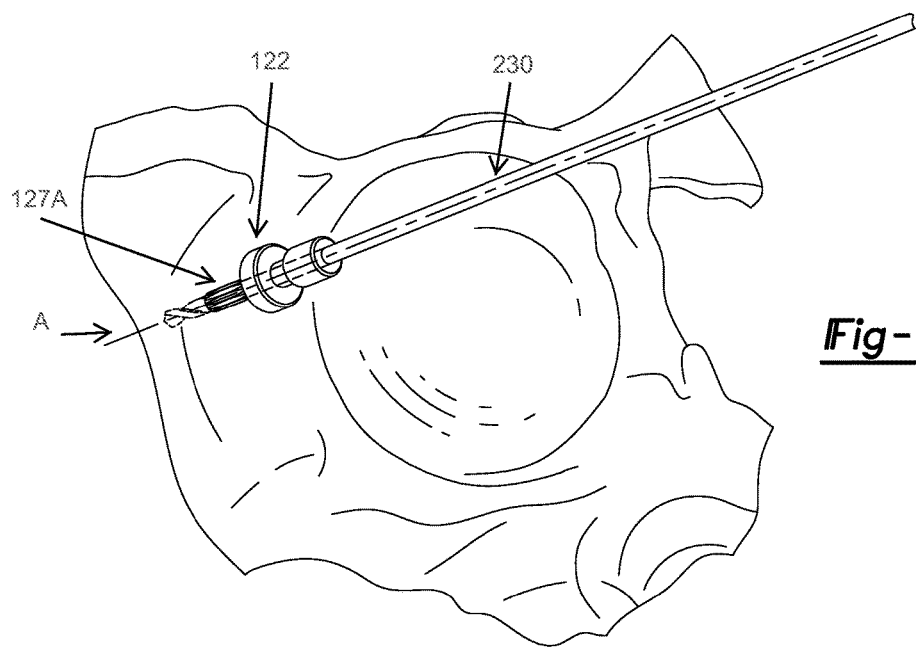

Once the alignment pin 230 is positioned within the pelvis 80, the drill insert 122 can be removed generally along the alignment pin 230 and the guide 100 can be removed longitudinally and/or laterally relative to the alignment pin 230. The alignment pin 230, either directly or indirectly, can then be used to guide various portions of a procedure, such as reaming of the acetabulum 82 and/or positioning the acetabular implant 250, as illustrated in FIG. 5. The acetabular implant 250 can be positioned in the acetabulum with reference to the alignment axis A by aligning the acetabular implant 250, having the central axis A', with the alignment pin 230. Accordingly, as illustrated in FIG. 5, the acetabular implant 250 can be positioned aligned with the alignment axis A that has been pre-planned and determined relative to the pelvis 80.

In various embodiments, the pin 230 may be positioned with the guide 100 and the drill insert 122 at a selected position (e.g. patient specific position) and maintained at the selected position for the remainder of the procedure. In various embodiments, however, the pin 230 may be removed and the drill insert or guide 122 may be maintained in the anatomy for an entire or remainder of the procedure. Further, as discussed herein, a first drill insert may be placed over the pin 230 and a second drill insert or guide may be placed at a second location. The second drill insert or guide may then be maintained in the anatomy for the remainder of the procedure while the guide 100 and the first drill insert 122 are removed.

Thus, additionally or alternatively, the alignment pin 230 may be selectively removable during selected procedures, such as a reaming of the acetabulum 82. As illustrated in FIG. 8, the drill insert 122 includes bone engaging fins 127a disposed on the distal portion 129. (It is noted that the drill insert 122 may alternatively include the self-tapping threads 127b, or other suitable anti-withdrawal features). As descried above, a surgeon may use a tool, such as the driver 500, to drive the drill insert 122 into bone at or near the acetabulum 82.

As described above, the fins 127a, and alternatively, the threads 127b, prevent withdrawal of the drill insert 122 from the bone. Accordingly, the alignment pin 230 may be selectively removed along the axis A without losing a reference to the alignment axis A. In other words, the drill insert 122 remains in the bone and provides a reference to the axis A after the alignment pin 230 has been removed. By removing the alignment pin 230, as needed or desired by the surgeon, the surgeon may ream, or perform other operative procedures unobstructed by the alignment pin 230.

Figure 9:
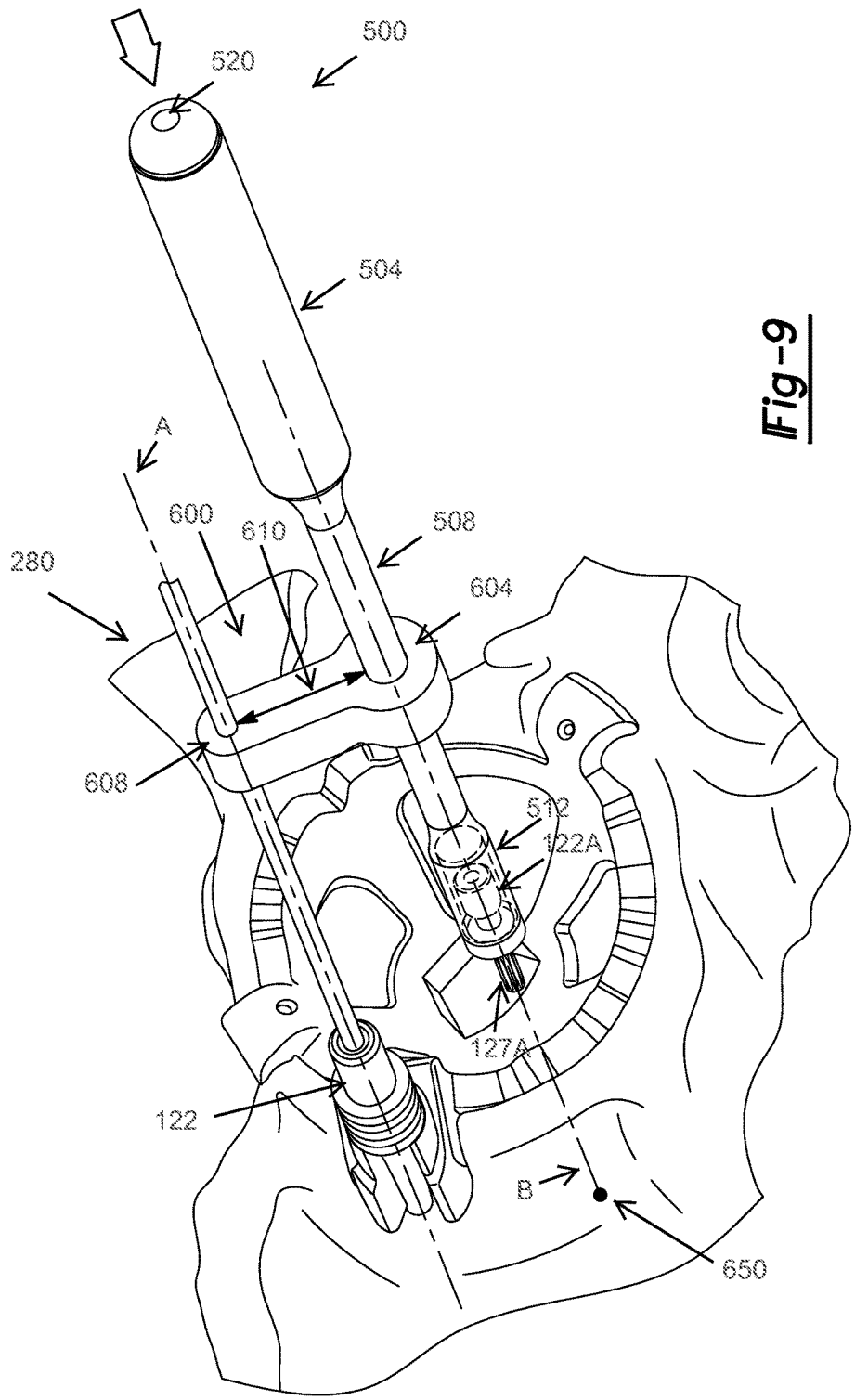
FIGS. 9-10 are isometric environmental views of FIG. 8 including a tool and coupler.

In yet another embodiment, the alignment pin 230 may be removed and assembled in an alternative drill insert 122 at a predefined area of bone near to the acetabulum 82, but at a location different from that defined by the drill insert 122 connected to the guide 100. As illustrated in FIG. 9, a coupling mechanism 600 may couple an alignment pin 230 to the driver 500.

The alignment pin 230 may be assembled to a first drill insert 122 according to any of the methods described above. In some scenarios, a surgeon may require an unobstructed workspace to ream the acetabulum 82 or perform other operational procedures. Accordingly, the surgeon may remove the alignment pin 230 from the first drill insert 122 as described above. Additionally or alternatively, the surgeon may relocate the alignment pin 230 to a preoperatively defined location so as to continue to guide various portions of a procedure, such as reaming of the acetabulum 82 and/or positioning the acetabular implant 250.

The coupling mechanism 600 may be formed to releasably couple two or more members, including the pin 230. The coupling mechanism, therefore, may include a first opening 604 configured to receive a portion of the shaft 508 and a second opening 608, a selected and formed distance 610 from the first opening 604, configured to receive a portion of the alignment pin 230. The distance 610 may be determined during the preoperative planning. For example, a distance 610 between the driver 500 and the alignment pin 230 may be selected so as to relocate the alignment pin 230, as will be described in detail below, at a predefined location relative to the acetabulum 82. Thus, the coupling mechanism may also be a patient specific coupling mechanism 600.

The driver 500 is configured to drive a second drill insert 122a, such as those described above. The alignment pin 230, via the coupling mechanism 600, acts as a guide for placement of the second drill insert 122a. The surgeon then drives the driver 500, such as with pushing, striking, or turning, about the axis A, via the coupling mechanism 600, until a suitable and/or predefined area of bone is selected. Thus, the guide 100 and the first drill insert 122 may be used to place pin 230. Following the positioning of the pin 230, the second drill insert 122a may be placed at a second location that is different than the location of the first drill insert 122.

For example, a second location 650 may be predetermined and/or selected during planning. The second location may be defined by the distance 610 and a selected orientation relative to the anatomy, such as aligned with the PSIS or ASIS. Thus, once the driver 500 is coupled to the pin 230 with the coupling mechanism 600, it may be aligned with the selected anatomy or other portion to be aligned along axis B with the second location 650. The driver 500 may then be used to place the second drill insert 122a at the second location 650.

Figure 10:
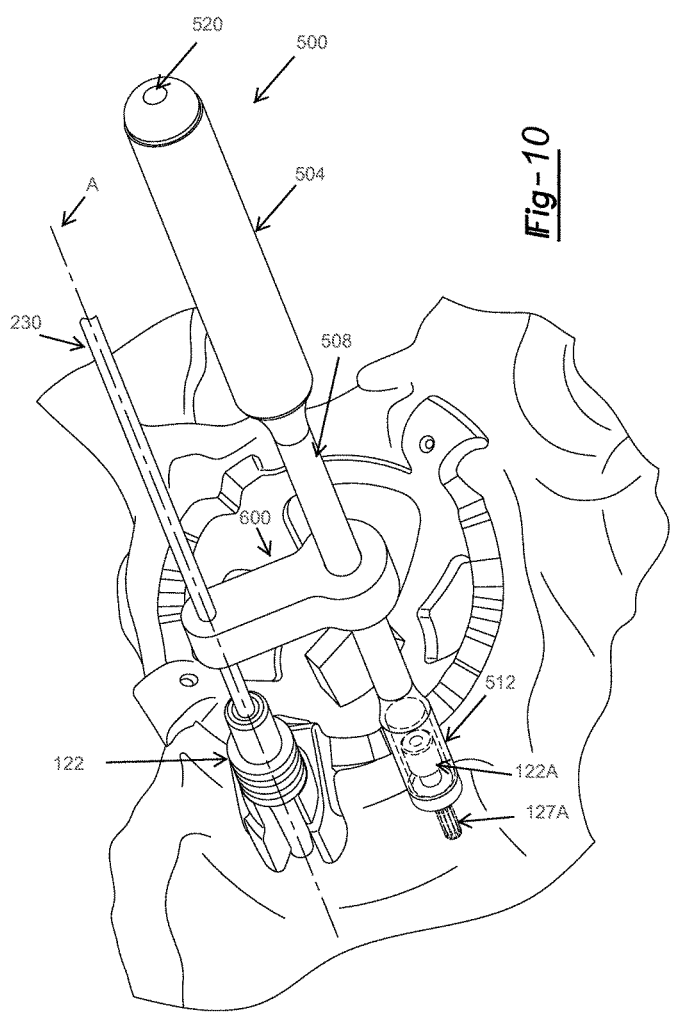
Figure 11A:
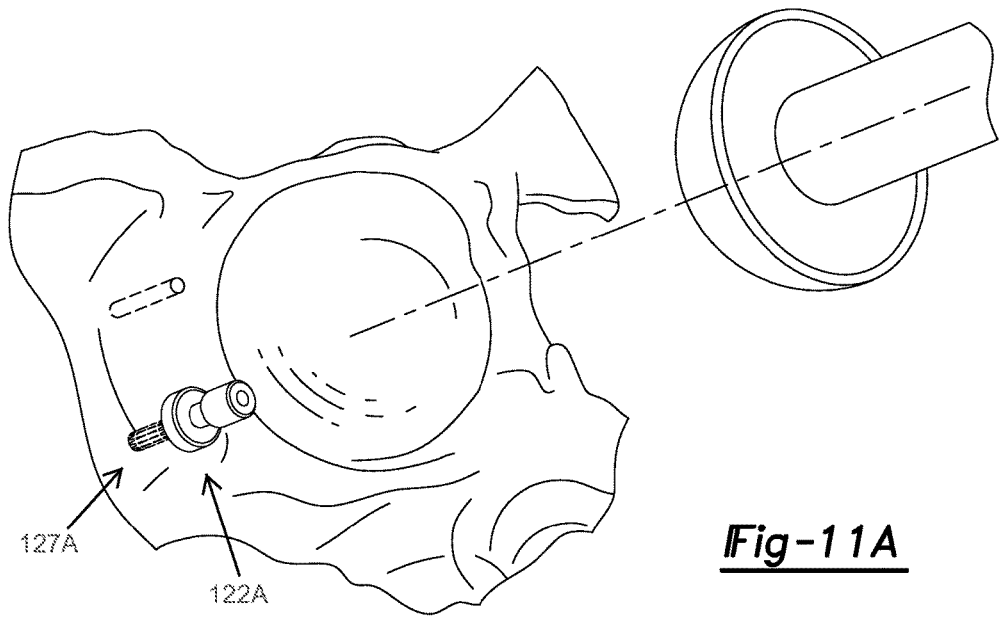
FIGS. 11A-11B are isometric environmental views of FIG. 8 illustrating a removal and reassembly of an alignment pin.

As illustrated in FIG. 10, the surgeon then drives the second drill insert 122a into the bone, as described above. It is noted that the second drill insert 122a may include fins 127a, threads 127b, or any other anti-withdrawal feature disposed on the distal portion 129. The surgeon may then remove the driver 500 from the second drill insert 122a as illustrated in FIG. 11A.

Figure 11B:
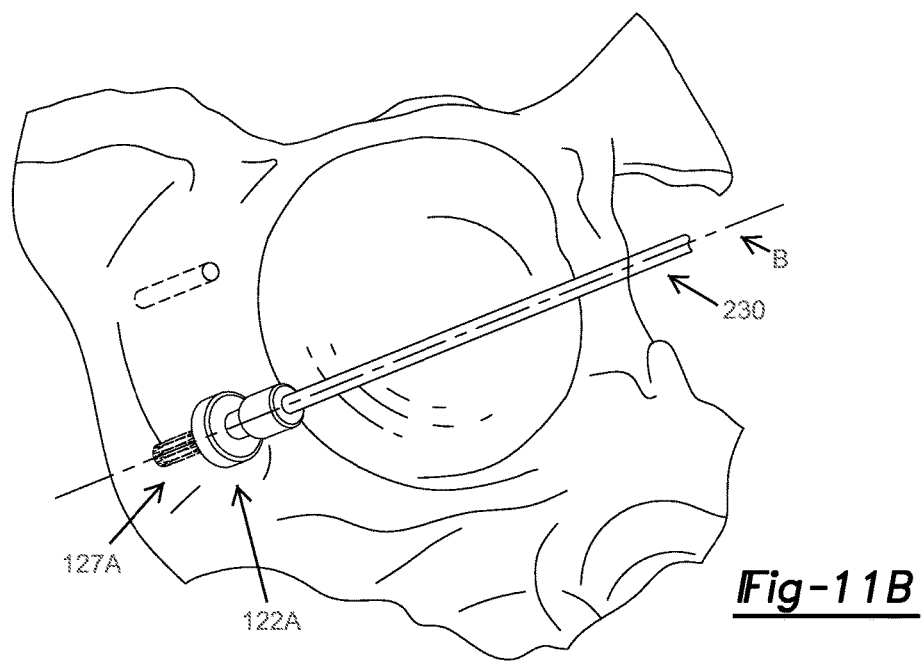

With additional reference to FIG. 11B, the surgeon may remove the alignment pin 230 from the first drill insert 122 and assemble the alignment pin 230 into the second drill insert 122a. In this manner, the alignment pin 230 may be removed from obstruction during operational procedures, such as reaming the acetabulum 82. Further, the alignment pin 230 may provide guidance, either directly or indirectly, while assembled in the second drill insert 122a, according to the predetermined plan, such as based on patient images. If selected, the surgeon may also remove the alignment pin 230 from the second drill insert 122a and reassemble the alignment pin 230 into the first drill insert 122. It is understood, therefore, that the drill inserts may be positioned for receiving the pin 230 as selected by the surgeon Further, the pin 230 may also be removed and reassembled into the second drill guide 122a as desired. Thus, the drill guide 122 may be fixed in bone separate from the guide 100 to allow for maintaining a location for placement of the pin 230, regardless of repeated removal and replacement of the pin 230. Also, it is understood that the pin 230 may define a guide axis, such as for reaming or implant placement, regardless of where it is placed. Thus, the pin 230 need not be in the drill insert 122 attached to the guide 100 to provide a guide axis, as discussed above, for performing portions of the procedure.

Moreover, it may be selected that the axis A defined through the drill insert 122 attached to the guide 100 may never be selected for performing alterations to the acetabulum, such as reaming or implant placement, but axis A may only be defined to guide placement of the second drill insert 122a for defining axis B to assist in the procedure. Thus, axis B may be used by a user, such as a surgeon, in a manner similar to axis A as described above.

It is understood that the patient-specific guide 100 can be positioned within the acetabulum 82 of the patient in a pre-planned and registered position. The positioning of the patient-specific guide 100 can require axial movement to and/or within the acetabulum 82 and rotational positioning within the acetabulum 82. The inserter 300 may be coupled relative to the central post 130, which is fixed to the acetabular guide 100 at a pre-planned and selected position, such that a post alignment axis 130a of the post 130 can be aligned with a pre-determined landmark. The inserter 300, including the alignment jig 310 or other appropriate alignment portion, can be aligned with a post alignment axis 130a of the central post 130 for viewing by a user. Viewing the alignment axis and/or the alignment jig 310 by the user during insertion of the guide 100 into the acetabulum 82 can allow the user to ensure appropriate positioning of the guide 100 within the acetabulum 82 by aligning the alignment jig 310 with a pre-determined landmark, such as the ASIS 410. Thus, the inserter 300 coupled in a keyed manner at a pre-determined orientation relative to the guide 100 can be used to assist in ensuring and placing the patient-specific guide 100 within the acetabulum 82.

According to various embodiments, when the guide 100 is placed in the acetabulum 82 in the predetermined location and orientation the guide 100 is registered to the acetabulum 82. Generally, the registration occurs and/or is achieved due to the contact of the outer surface 104 with the acetabulum either alone or with the various surfaces of the registration hooks 110 and/or the surface 128. Thus, the guide 100 can be registered to the acetabulum 82 of a specific patient in a specific and predetermined location and orientation.

Various patient-specific guides, secondary guides, reamers, guide handles, inserters, impactors, support devices, electronic positioners and other instruments can be used in various combinations and based on surgeon preferences or patient and preoperative or intraoperative circumstances for preparing an acetabulum and guiding and implanting an acetabular implant along a preoperatively determined alignment orientation. In this respect, tools and instrumentation providing redundant functionality and of different embodiments may provide to the surgeon in a kit or per surgeon's request.

For example, adaptors and other instruments described above can be provided and used in various combinations within the scope of the methods described herein.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. An acetabular guide system for placing a guide pin near an acetabulum, comprising:
    a patient specific acetabular guide including an interior surface and an exterior surface, the exterior surface being configured to have a geometry to register within the acetabulum of a specific patient;
    an alignment drill insert configured to be received by the patient specific acetabular guide at a first location, the alignment drill insert having a first longitudinal bore configured to be received concentrically in a guide bore of the patient specific acetabular guide, the guide bore extending exterior to the interior surface;
    an anchored drill insert including at least one anti-withdrawal feature, such that the anchored drill insert is configured to be fixed to a boney portion exterior to the acetabulum at a second location a predetermined distance from the first location, the anchored drill insert forming a second longitudinal bore;
    an alignment pin configured to be received by the first longitudinal bore; and
    a coupler configured to couple the alignment pin to a driver, wherein the coupler is dimensioned to correspond to the predetermined distance between the first location and the second location, such that the driver can place the anchored drill insert at the second location based on the first location of the alignment drill insert.

2. The acetabular guide system of claim 1, wherein the anchored drill insert includes a proximal portion and a distal portion, the distal portion including the at least one anti-withdrawal feature.

3. The acetabular guide of claim 2, wherein the at least one anti-withdrawal feature includes at least one of a thread and a fin extending from an exterior surface of the distal portion.

4. The acetabular guide of claim 2, wherein the proximal portion is engageable by the driver, the driver being configured to rotate the proximal portion thereby driving the distal portion into the boney portion exterior to the acetabulum.

5. The acetabular guide system of claim 4, wherein the driver is rotated via the coupler around the alignment pin to a predetermined location relative to the acetabulum.

6. The acetabular guide system of claim 5, wherein the alignment pin is configured to be selectively removed from the alignment drill insert and assembled to the anchored drill insert.

7. A method of placing a guide pin near an acetabulum with an acetabular guide system, comprising:
    providing a patient specific acetabular guide including forming an exterior surface of the patient specific acetabular guide to have a geometry to register within the acetabulum of a specific patient;
    providing an alignment drill insert having a first longitudinal bore configured to be received concentrically in a guide bore of the patient specific acetabular guide, the guide bore extending exterior to an interior surface of the patient specific acetabular guide to align the alignment drill insert at a first location;
    providing an anchored drill insert including a second longitudinal bore and at least one anti-withdrawal feature, such that the anchored drill insert is configured to be fixed to a boney portion at a second location a predefined distance from the first location;
    providing an alignment pin configured to be received by the first longitudinal bore; and
    providing a coupler configured to couple the alignment pin to a driver, wherein the coupler is dimensioned to correspond to the predetermined distance between the first location and the second location, such that the driver can place the anchored drill insert at the second location based on the first location of the alignment drill insert.

8. The method of claim 7, wherein forming the exterior surface of the patient specific acetabular guide configured to have a geometry to register within the acetabulum of a specific patient includes acquiring images of the specific patient and designing the exterior surface of the patient specific acetabular guide to have a mating surface with the acetabulum of the specific patient.

9. The method of claim 7, wherein providing the anchored drill insert includes providing a proximal portion and providing the at least one anti-withdrawal feature on a distal portion.

10. The method of claim 9, further comprising engaging the proximal portion by the driver in order to drive the distal portion into the boney portion at the second location and assembling the alignment pin into the anchored drill insert.

11. The method of claim 10, further comprising selectively removing the alignment pin from the anchored drill insert while maintaining the anchored drill insert in the boney portion.

12. The method of claim 9, further comprising coupling the alignment pin to the driver configured to drive the anchored drill insert into the boney portion at the second location at the predefined distance from the first location.

13. The method of claim 12, further comprising driving, via the driver, the anchored drill insert into the boney portion at the second location.

14. The method of claim 13, further comprising selectively removing the alignment pin from the alignment drill insert and positioning the alignment pin into the anchored drill insert.

15. A method for implanting an acetabular implant, comprising:
   forming a patient specific acetabular guide having an exterior surface with a geometry formed to register within an acetabulum of a specific patient;
   connecting an alignment drill insert to the patient specific acetabular guide at a first location relative to the acetabulum, the alignment drill insert having a first longitudinal bore configured to be received concentrically in a guide bore of the patient specific acetabular guide, the guide bore extending exterior to the interior surface to align the first drill insert at a first location;
   removably fixing an alignment pin to a first portion of bone at the first location, the alignment pin being received by the first longitudinal bore;
   coupling a driver to the alignment pin via a coupler;
   driving, using the driver, an anchored drill insert, including a second longitudinal bore and an anti-withdrawal feature, into a second portion of bone at a second location, the second location being at a predetermined distance from the first location; and
   selectively removing the alignment pin from the alignment drill insert.

16. The method of claim 15, further comprising removably fixing the alignment pin to the second portion of bone at the second location, the alignment pin being received by the second longitudinal bore.

17. The method of claim 16, further comprising selectively removing the alignment pin from the anchored drill insert.

18. The method of claim 17, further comprising reaming the acetabulum after removing the alignment pin from the alignment drill insert.

19. The method of claim 18, further comprising inserting the alignment pin, after reaming the acetabulum, through the second longitudinal bore of the anchored drill insert.

20. The method of claim 19, further comprising implanting an acetabular implant into the reamed acetabulum based on an axis defined by the alignment pin.

* * * * *